(12) United States Patent
Melsheimer

(10) Patent No.: US 12,349,893 B2
(45) Date of Patent: Jul. 8, 2025

(54) IMPLANTABLE TISSUE ANCHORS, KITS THAT INCLUDE A TISSUE ANCHOR, AND RELATED METHODS OF TREATMENT

(71) Applicant: Cook Medical Technologies LLC, Bloomington, IN (US)

(72) Inventor: Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 573 days.

(21) Appl. No.: 17/680,197

(22) Filed: Feb. 24, 2022

(65) Prior Publication Data

US 2022/0265262 A1    Aug. 25, 2022

Related U.S. Application Data

(60) Provisional application No. 63/153,414, filed on Feb. 25, 2021.

(51) Int. Cl.
*A61B 17/04* (2006.01)
*A61B 17/122* (2006.01)
*A61B 17/00* (2006.01)

(52) U.S. Cl.
CPC ...... *A61B 17/0401* (2013.01); *A61B 2017/00831* (2013.01); *A61B 2017/0416* (2013.01); *A61B 2017/0429* (2013.01)

(58) Field of Classification Search
CPC ... A61B 17/0401; A61B 17/08; A61B 17/083; A61B 17/10; A61B 17/11; A61B 17/12;
(Continued)

(56) References Cited

U.S. PATENT DOCUMENTS

| | | |
|---|---|---|
| 4,494,531 A | 1/1985 | Gianturco |
| 4,832,055 A | 5/1989 | Palestrant |

(Continued)

FOREIGN PATENT DOCUMENTS

| | | |
|---|---|---|
| AU | 2009309026 | 5/2010 |
| EP | 2106752 | 10/2009 |

(Continued)

OTHER PUBLICATIONS

European Patent Office, Examination report mailed on Apr. 13, 2017 for European patent application No. 10706443.8.

(Continued)

*Primary Examiner* — Kathleen S Holwerda
(74) *Attorney, Agent, or Firm* — MacMillan, Sobanski & Todd, LLC

(57) ABSTRACT

Example implantable tissue anchors, kits that include an implantable tissue anchor, and associated methods are described. An example implantable tissue anchor is moveable between a first, expanded configuration and a second, compressed configuration. The implantable tissue anchor has a first end, a second end, and a main body. The main body defines a first arm, a second arm, a first plurality of recesses on the first arm, a first plurality of barbs on the first arm, a second plurality of recess on the second arm, and a second plurality of barbs on the second arm. The first arm and the second arm define a first closed loop and a first passageway that extends through the main body when the implantable tissue anchor is in the first, expanded configuration.

18 Claims, 18 Drawing Sheets

(58) Field of Classification Search
CPC . A61B 17/122; A61B 17/1227; A61B 17/128; A61B 17/1285; A61B 17/0487; A61B 17/06166; A61B 2017/06176; A61B 2017/00831; A61B 2017/0416; A61B 2017/0429

USPC ....... 606/142, 151, 157, 158, 216, 219, 221, 606/228–232

See application file for complete search history.

(56) References Cited

U.S. PATENT DOCUMENTS

| | | | |
|---|---|---|---|
| 4,994,077 | A | 2/1991 | Dobben |
| 5,236,440 | A * | 8/1993 | Hlavacek ........... A61B 17/0644 606/213 |
| 5,324,304 | A | 6/1994 | Rasmussen |
| 5,607,465 | A | 3/1997 | Camilli |
| 6,200,336 | B1 | 3/2001 | Pavcnik et al. |
| 6,391,045 | B1 | 5/2002 | Kim et al. |
| 6,623,506 | B2 | 9/2003 | McGuckin, Jr. et al. |
| 6,706,054 | B2 | 3/2004 | Wessman et al. |
| 6,783,538 | B2 | 8/2004 | McGuckin, Jr. et al. |
| 7,128,759 | B2 | 10/2006 | Osborne et al. |
| 7,303,571 | B2 | 12/2007 | Makower et al. |
| 7,361,189 | B2 | 4/2008 | Case et al. |
| 7,569,071 | B2 | 8/2009 | Haverkost et al. |
| 7,582,100 | B2 | 9/2009 | Johnson et al. |
| 7,799,042 | B2 * | 9/2010 | Williamson, IV ..... A61B 17/32 606/213 |
| 7,806,908 | B2 | 10/2010 | Ruff |
| 8,074,655 | B2 | 12/2011 | Sanders |
| 8,109,990 | B2 | 2/2012 | Paul et al. |
| 8,167,787 | B2 | 5/2012 | Gillis |
| 8,273,105 | B2 | 9/2012 | Cohen et al. |
| 8,475,516 | B2 | 7/2013 | Paul et al. |
| 8,652,197 | B2 | 2/2014 | Paul et al. |
| 8,932,327 | B2 | 1/2015 | Kosa et al. |
| 8,932,328 | B2 | 1/2015 | Megaro et al. |
| 8,956,372 | B2 | 2/2015 | Fenton et al. |
| 8,968,362 | B2 | 3/2015 | Thomas et al. |
| 9,078,748 | B2 | 6/2015 | Paul et al. |
| 9,675,341 | B2 | 6/2017 | D'Agostino et al. |
| 9,833,234 | B2 | 12/2017 | Broom et al. |
| 9,855,034 | B2 | 1/2018 | Broom et al. |
| 10,143,544 | B2 | 12/2018 | Paul et al. |
| 10,398,427 | B2 | 9/2019 | Dineen et al. |
| 10,470,755 | B2 | 11/2019 | Broom et al. |
| 10,492,780 | B2 | 12/2019 | Gross et al. |
| 10,729,421 | B2 | 8/2020 | Stone et al. |
| 2001/0039450 | A1 | 11/2001 | Pavcnik et al. |
| 2003/0163159 | A1 | 8/2003 | Patel et al. |
| 2005/0080454 | A1 * | 4/2005 | Drews ................. A61B 17/083 606/151 |
| 2005/0187614 | A1 | 8/2005 | Agnew |
| 2005/0267513 | A1 | 12/2005 | Osborne et al. |
| 2006/0241675 | A1 | 10/2006 | Johnson et al. |
| 2006/0282104 | A1 * | 12/2006 | Williamson ........... A61B 17/32 606/151 |
| 2007/0005095 | A1 | 1/2007 | Osborne et al. |
| 2007/0112423 | A1 | 5/2007 | Chu |
| 2008/0046071 | A1 | 2/2008 | Pavcnik |
| 2008/0140110 | A1 | 6/2008 | Spence |
| 2008/0262542 | A1 | 10/2008 | Sulamanidze et al. |
| 2009/0228040 | A1 * | 9/2009 | Mas ................... A61B 17/0057 606/219 |
| 2009/0234434 | A1 | 9/2009 | Johnson et al. |
| 2009/0248066 | A1 | 10/2009 | Wilkie |
| 2009/0248070 | A1 | 10/2009 | Kosa et al. |
| 2009/0306681 | A1 | 12/2009 | Del Nido et al. |
| 2010/0217381 | A1 | 8/2010 | Paul et al. |
| 2012/0130476 | A1 | 5/2012 | Paul et al. |
| 2012/0253388 | A1 | 10/2012 | Gleiman |
| 2013/0289709 | A1 | 10/2013 | Paul et al. |
| 2014/0155987 | A1 | 6/2014 | Paul et al. |
| 2014/0309631 | A1 | 10/2014 | McLawhorn et al. |
| 2015/0066078 | A1 | 3/2015 | Broom et al. |
| 2015/0094525 | A1 | 4/2015 | Tomc et al. |
| 2016/0213371 | A1 * | 7/2016 | Miraki .................... A61B 1/05 |
| 2018/0318114 | A1 | 11/2018 | Huang et al. |
| 2019/0254799 | A1 | 8/2019 | Amson et al. |
| 2020/0046337 | A1 | 2/2020 | Dreyfuss |

FOREIGN PATENT DOCUMENTS

| | | |
|---|---|---|
| WO | 2007133103 | 11/2007 |
| WO | 2009088957 | 7/2009 |
| WO | 2010099209 | 9/2010 |
| WO | 2019237071 | 12/2019 |

OTHER PUBLICATIONS

International Searching Authority, The International Search Report And Written Opinion of the International Searching Authority, May 20, 2010, for International Application No. PCT/US2010/025245.

Complete Prosecution History, Patent No. 8,652, 197, Compiled Feb. 6, 2014.

Complete Prosecution History, Patent No. 8,475,516, Compiled Feb. 6, 2014.

Complete Prosecution History, Patent No. 8, 109,990, Compiled Feb. 6, 2014.

Volcano Corporation, "Crux: Vena Cava Filter," www.volcanocorp.com, Brochure, pp. 1-2, retrieved Aug. 26, 2014.

* cited by examiner

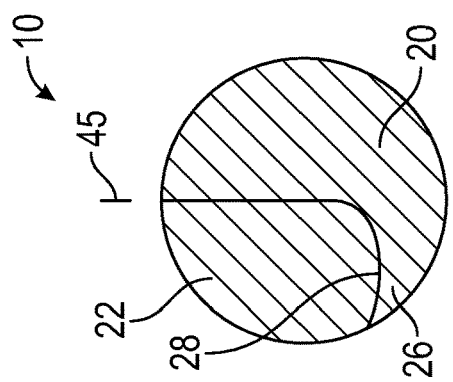
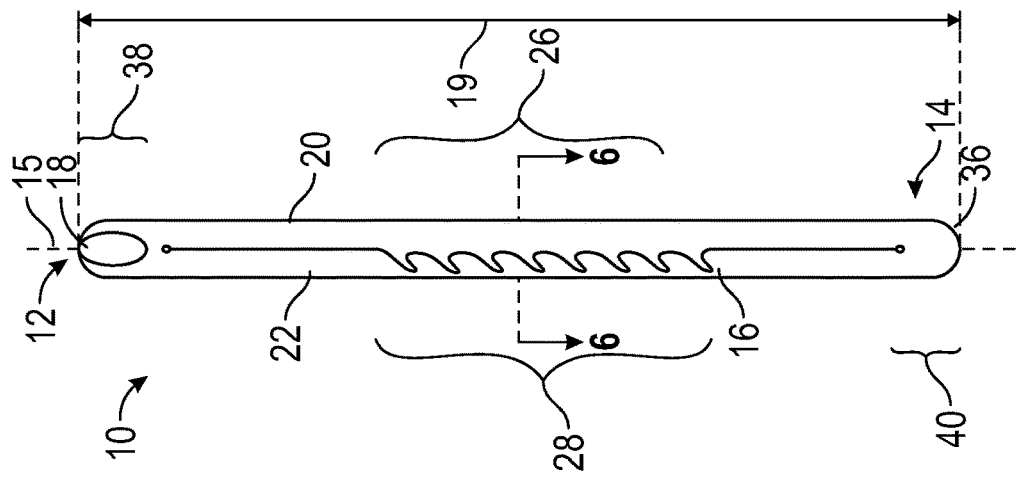
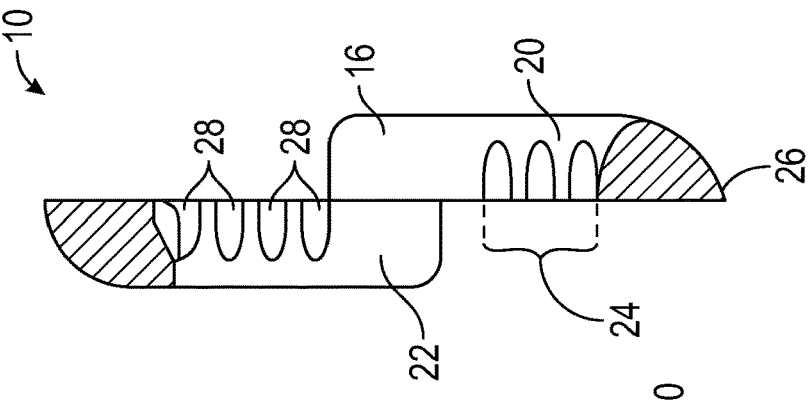
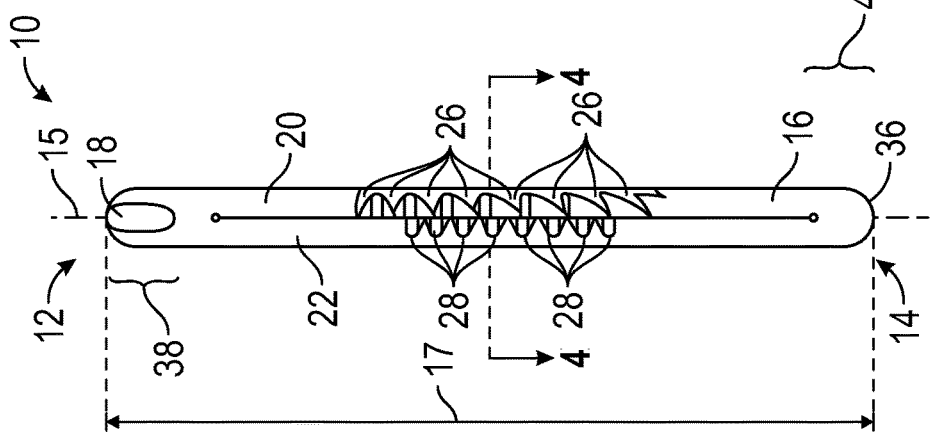
FIG. 6
FIG. 5
FIG. 4
FIG. 3

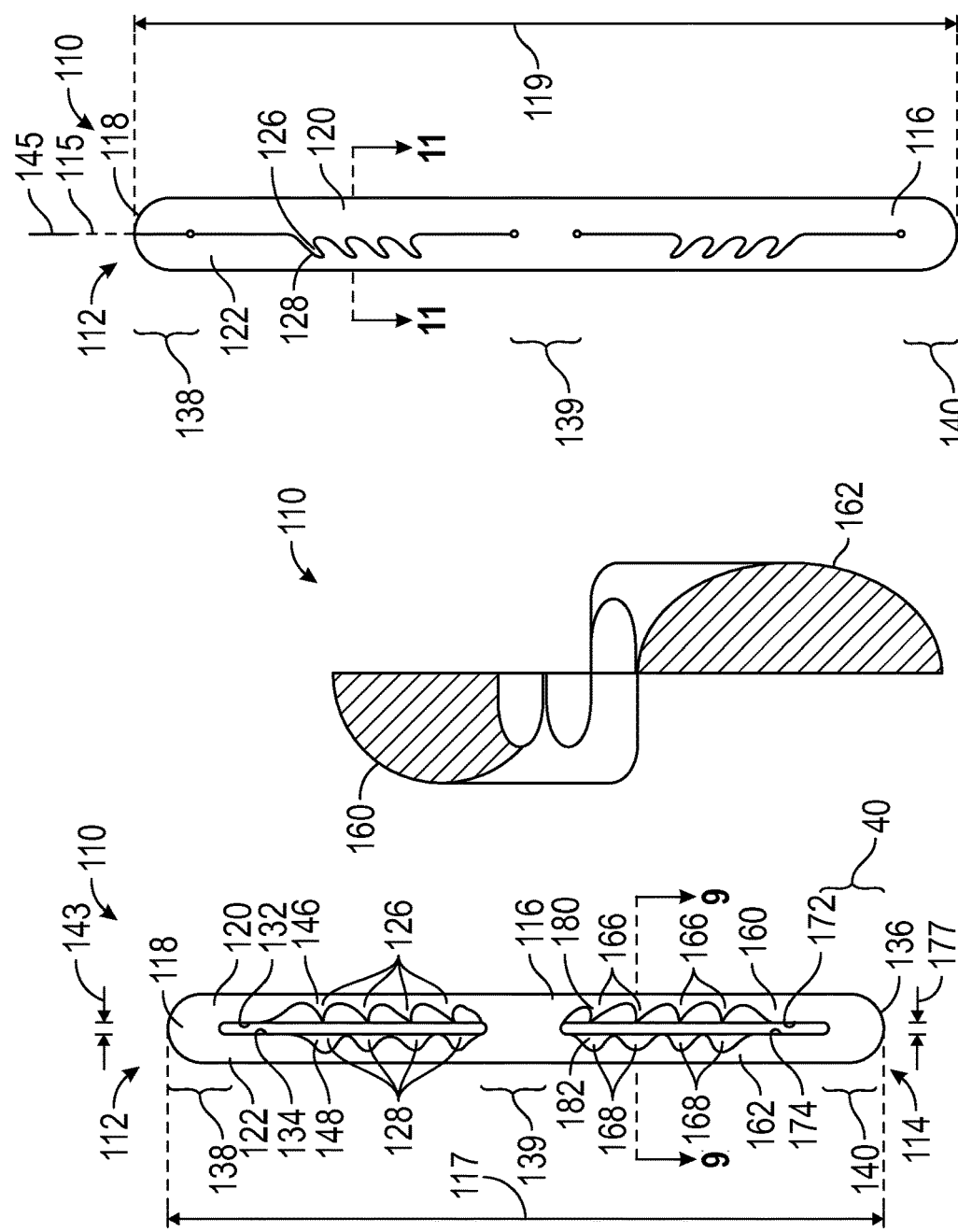
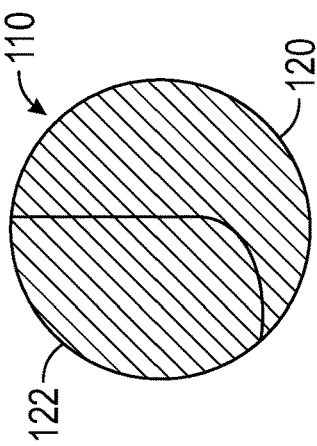
FIG. 11
FIG. 10
FIG. 9
FIG. 8

IMPLANTABLE TISSUE ANCHORS, KITS THAT INCLUDE A TISSUE ANCHOR, AND RELATED METHODS OF TREATMENT

RELATED APPLICATIONS

This application claims priority to U.S. Provisional Application No. 63/153,414, filed Feb. 25, 2021. The entire contents of this related application are hereby incorporated by reference into this disclosure.

FIELD

The disclosure relates generally to the field of medical devices. More particularly, the disclosure relates to implantable tissue anchors, kits that include an implantable tissue anchor, and related methods of treatment.

BACKGROUND

It is sometimes necessary or desirable to secure tissue or a portion of a tissue within the body of an animal, such as a human, in a manner that temporarily or permanently adjusts a position or orientation of the tissue or the portion of a tissue. For example, in the treatment of benign prostatic hyperplasia, it may be desirable to adjust the position of one or more tissues or portions of tissue, such as the prostate, to provide treatment. In another example, in the treatment of Obstructive Sleep Apnea (OSA), it may be desirable to adjust the position of one or more tissues or portions of tissue, such as the soft palate, to provide treatment.

Benign prostatic hyperplasia is a condition in which the flow of urine is blocked due to the enlargement of the prostate gland. To prevent complications and relieve symptoms, current devices are implanted trans-urethrally and tie an interior wall of the prostate to an exterior wall of the prostate to widen the urethra. These devices generally are formed of multiple materials and utilize two intersections between three different pieces of material, which increases manufacturing costs. In addition, these devices generally have a fixed length and require full perforation of the urethra and prostate walls, which increases the complexity associated with delivering the devices. Furthermore, these devices may not be able to perforate the entire urethra and prostate walls if introduced at angles less than 90 degrees or within tissue that has a thickness greater than the length of the device.

OSA is a clinical disorder in which a partial or complete collapse of soft tissue occurs in the airway during sleep. This leads to a blockage of the airway and impaired breathing during sleep. Mild OSA can lead to fatigue, reduced alertness following sleep, and a general reduction in productivity for the affected individual. Severe OSA can lead to sleep deprivation, hypoxemia, and depression.

The art provides various options for the treatment of OSA. Continuous Positive Airway Pressure (CPAP) machines, which supply positive air pressure through a facemask and into the airway during sleep, are used most frequently. The positive air pressure maintains an open airway to prevent apnea and snoring. While these machines are generally considered effective, they are bulky, noisy, and cumbersome to use. Furthermore, use of these machines can be socially awkward for some individuals. Oral appliances that force the jaw forward to maintain an open airway can also be used. These devices are generally considered to be not as effective as CPAP machines, and can be uncomfortable to use. Furthermore, these devices are frequently ejected from the mouth during sleep, reducing their effectiveness over the entire course of a sleeping period. Invasive surgical procedures can also be used to treat OSA. Various techniques have been described, including uvulopalatopharyngoplasty (UPPP), maxillomandibular advancement (MMA), and even tracheostomy. Surgical procedures are generally considered to have limited and potentially short-lived effectiveness. Furthermore, many of the procedures require hospitalization and the use of general anesthesia. As a result, these procedures are generally reserved for severe cases of OSA.

A need exists, therefore, for new and improved devices for adjusting tissue within the body, kits that include a device for adjusting tissue within the body, and methods of adjusting tissue within the body.

SUMMARY OF SELECTED EXAMPLE EMBODIMENTS

Various example implantable tissue anchors, kits that include an implantable tissue anchor, and related methods of treatment are described herein.

An example implantable tissue anchor is moveable between a first, expanded configuration and a second, compressed configuration. The implantable tissue anchor has a first end, a second end, and a main body. The main body defines a first arm, a second arm, a first plurality of recesses on the first arm, a first plurality of barbs on the first arm, a second plurality of recesses on the second arm, and a second plurality of barbs on the second arm. The first arm and the second arm define a first closed loop and a first passageway that extends through the main body when the implantable tissue anchor is in the first, expanded configuration. A first barb of the first plurality of barbs is partially disposed within a first recess of the second plurality of recesses when the implantable tissue anchor is in the second, compressed configuration. A first barb of the second plurality of barbs is partially disposed within a first recess of the first plurality of recesses when the implantable tissue anchor is in the second, compressed configuration.

Another example implantable tissue anchor is moveable between a first, expanded configuration and a second, compressed configuration. The implantable tissue anchor has a first end, a second end, and a main body. The main body defines a first arm, a second arm, a third arm, a fourth arm, a first plurality of recesses on the first arm, a first plurality of barbs on the first arm, a second plurality of recess on the second arm, a second plurality of barbs on the second arm, a third plurality of recesses on the third arm, a third plurality of barbs on the third arm, a fourth plurality of recess on the fourth arm, and a fourth plurality of barbs on the fourth arm. The first arm and the second arm define a first closed loop and a first passageway that extends through the main body when the implantable tissue anchor is in the first, expanded configuration. The third arm and the fourth arm define a second closed loop and a second passageway that extends through the main body when the implantable tissue anchor is in the first, expanded configuration. A first barb of the first plurality of barbs is partially disposed within a first recess of the second plurality of recesses when the implantable tissue anchor is in the second, compressed configuration. A first barb of the second plurality of barbs is partially disposed within a first recess of the first plurality of recesses when the implantable tissue anchor is in the second, compressed configuration. A first barb of the third plurality of barbs is partially disposed within a first recess of the fourth plurality of recesses when the implantable tissue anchor is in the second, compressed configuration. A first barb of the fourth plurality of barbs is partially disposed within a first recess of the third plurality of recesses when the implantable tissue anchor is in the second, compressed configuration. The main body has a first length in the first, expanded configuration and a second length in the second, compressed configuration that is greater than the first length.

An example method of adjusting tissue within a body comprises: introducing a delivery device into a bodily passage, the delivery device includes an outer sheath, an access sheath partially disposed within the outer sheath, a flexible pusher partially disposed within the access sheath, an implantable tissue anchor disposed distal to the flexible pusher and within the access sheath, and a suture that has a first end, a second end, is attached to the implantable tissue anchor and disposed through the flexible pusher; applying a force on the delivery device such that the delivery device is advanced toward a point of treatment; applying a distally-directed force on the access sheath while maintaining the position of the outer sheath such that the access sheath is advanced distally relative to the outer sheath and creates an incision in the tissue defining the bodily passage; continuing the application of the distally-directed force on the access sheath while maintaining the position of the outer sheath such that the access sheath advances into the tissue; applying a distally-directed force on the flexible pusher while maintaining the position of the access sheath such that the tissue anchor advances out of the access sheath and into the tissue a distance equal to about ½ the length of the tissue anchor; applying a proximally-directed force on the access sheath and the flexible pusher such that the access sheath and the flexible pusher are partially withdrawn from the tissue and tension is applied to the tissue anchor via the suture; applying a proximally-directed force on the access sheath while maintaining the position of the flexible pusher until the tissue anchor becomes free of the access sheath and is disposed within the tissue in the first, expanded configuration; releasing the first end of the suture from attachment to the implantable tissue anchor; applying a proximally-directed force on the second end of the suture such that it becomes free of attachment to the tissue anchor; applying a proximally-directed force on the access sheath and the flexible pusher such that the access sheath and the flexible pusher are withdrawn into the outer sheath; applying a proximally-directed force on the delivery device such that the outer sheath, access sheath, flexible pusher, and suture are withdrawn from the bodily passage.

An example kit that includes an implantable tissue anchor includes a first implantable tissue anchor; a second implantable tissue anchor; a third implantable tissue anchor; a fourth implantable tissue anchor; a delivery device for deploying an implantable tissue anchor; and instructions for use.

Additional understanding of these example implantable tissue anchors, kits, and methods can be obtained by review of the detailed description, below, and the appended drawings.

BRIEF DESCRIPTION OF THE DRAWINGS

FIG. 3 is a side view of the tissue anchor illustrated in FIG. 1.

FIG. 4 is a cross-sectional view of the tissue anchor illustrated in FIG. 3 taken along line 4-4.

FIG. 5 is another side view of the tissue anchor illustrated in FIG. 1. The tissue anchor is shown in a second, compressed configuration.

FIG. 6 is a cross-sectional view of the tissue anchor illustrated in FIG. 5 taken along line 6-6.

FIG. 8 is a side view of the tissue anchor illustrated in FIG. 7.

FIG. 9 is a cross-sectional view of the tissue anchor illustrated in FIG. 8 taken along line 9-9.

FIG. 10 is another side view of the tissue anchor illustrated in FIG. 7. The tissue anchor is shown in a second, compressed configuration.

FIG. 11 is a cross-sectional view of the tissue anchor illustrated in FIG. 10 taken along line 11-11.

FIG. 2.5 is a partial elevation view of a delivery device disposed within a bodily passage and partially disposed within tissue. The implantable tissue anchor is in the first, expanded configuration.

DETAILED DESCRIPTION OF SELECTED EXAMPLES

Figure 1:
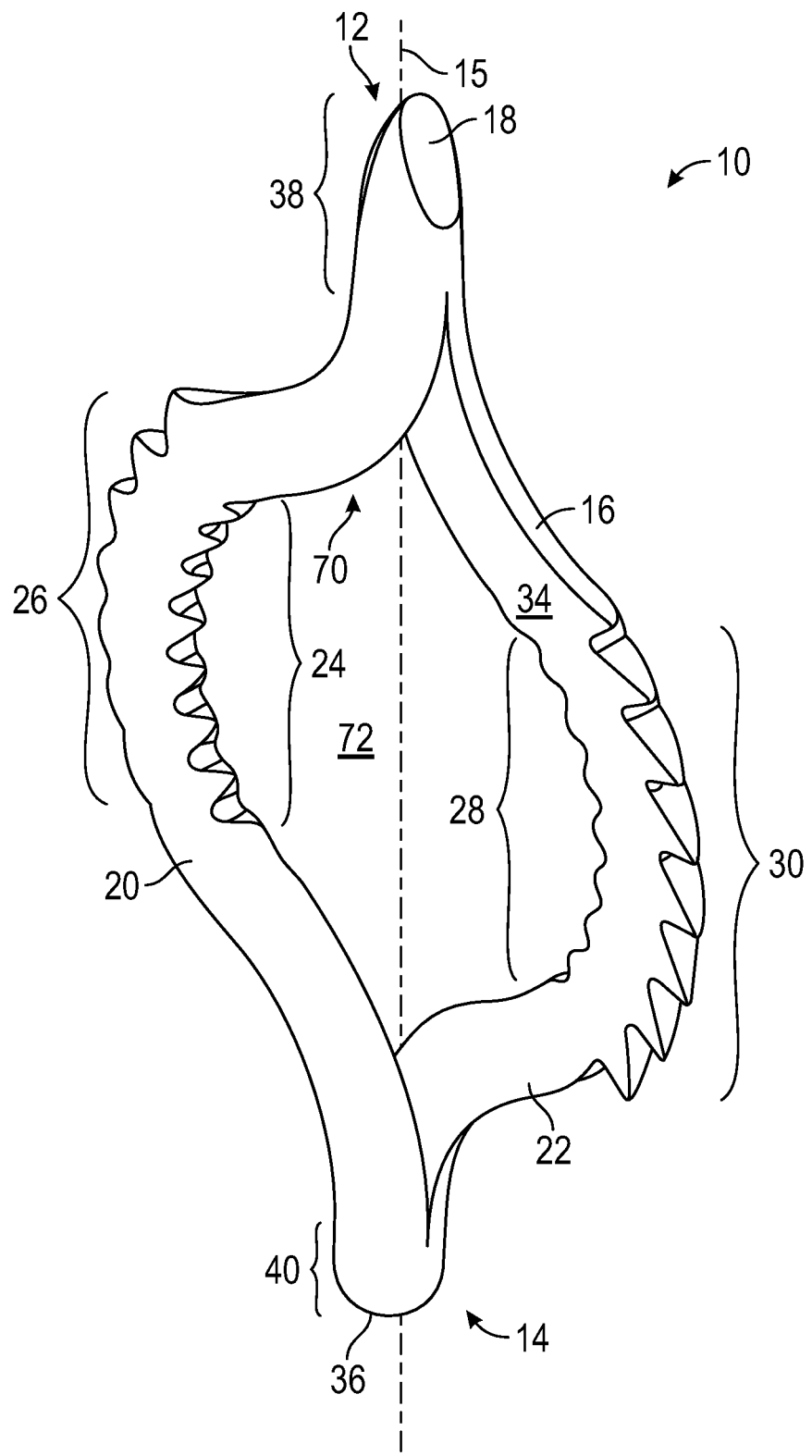
FIG. 1 is a perspective view of a first example implantable tissue anchor. The tissue anchor is shown in a first, expanded configuration.

The following detailed description and the appended drawings describe and illustrate various example implantable tissue anchors, kits that include an implantable tissue anchor, and related methods of treatment. The description and illustration of these examples are provided to enable one skilled in the art to make and use an implantable tissue anchor, a kit that includes an implantable tissue anchor, and to practice a method of treatment using an implantable tissue anchor. They are not intended to limit the scope, of the invention, or the protection sought, in any manner. The invention is capable of being practiced or carried out in various ways and the examples described and illustrated herein are merely selected examples of the various ways of practicing or carrying out the invention and are not considered exhaustive.

FIGS. 1, 2, 3, 4, 5, and 6 illustrate a first example implantable tissue anchor 10 that is movable between a first, expanded configuration, as shown in FIGS. 1, 2, 3, and 4, and a second, compressed configuration, as shown in FIGS. 5 and 6.

The tissue anchor 10 has a first end 12, a second end 14, a lengthwise axis 15, and a main body 16 that defines a cutting tip 18 on the first end 12, a first arm 20, a second arm 22, a first plurality of recesses 24 on the first arm 20, a first plurality of barbs 26 on the first arm 20, a second plurality of recesses 28 on the second arm 22, a second plurality of barbs 30 on the second arm 22, a first planar surface 32, a second planar surface 34, and a blunt tip 36 on the second end 14. The main body 16 of the tissue anchor 10 has a first length 17 in the first, expanded configuration and a second length 19 in the second, compressed configuration that is greater than the first length 17. The first arm 20 and the second arm 22 terminate in a proximal terminus 38 and a distal terminus 40. The first planar surface 32 is defined on the first arm 20 and has a central portion 42 disposed between the first and second ends 12, 14 and the second planar surface 34 is defined on the second arm 22 and has a central portion 44 disposed between the first and second ends 12, 14.

In the first, expanded configuration the first plurality of barbs 26 is free of the second plurality of recesses 28, the second plurality of barbs 30 is free of the first plurality of recesses 24, and the central portion 42 of the first planar surface 32 is disposed a first distance 43 from the central portion 44 of the second planar surface 34. In the second, compressed configuration each barb of the first plurality of barbs 26 is partially disposed within a distinct recess of the second plurality of recesses 28, each barb of the second plurality of barbs 30 is partially disposed within a distinct recess of the first plurality of recesses 24, and the central portion 42 of the first planar surface 32 is disposed a second distance 45 from the central portion 44 of the second planar surface 34 that is less than the first distance 43. In the illustrated embodiment, in the second, compressed configuration a first barb 46 of the first plurality of barbs 26 is partially disposed within a first recess 48 of the second plurality of recesses 28, a first barb 50 of the second plurality of barbs 30 is partially disposed within a first recess 52 of the first plurality of recesses 24, and the first planar surface 32 is disposed adjacent to and contacts the second planar surface 34 (e.g., along the central portions 42, 44).

Each barb of the first plurality of barbs 26 and the second plurality of barbs 30 has a face 54, a flank 56, a tip 58, and a gullet 60. In the first, expanded configuration the face 54 of a first set 62 of the first and second plurality of barbs 26, 30 is directed away from the first end 12 of the implantable tissue anchor 10 and the face 54 of a second set 64 of the first and second plurality of barbs 26, 30 is directed toward the second end 14 of the implantable tissue anchor 10. In the expanded configuration the flank 56 of a first barb 66 of each of the first and second plurality of barbs 26, 30 is disposed at a first angle 67 relative to the lengthwise axis 15 of the implantable tissue anchor 10 and the flank 56 of a second barb 68 of each of the first and second plurality of barbs 26, 30 is disposed at a second angle 69 relative to the lengthwise axis 15 of the implantable tissue anchor 10. The first angle 67 is greater than 90 degrees and the second angle 69 is greater than the first angle 67 (e.g., greater than 135 degrees). However, alternative embodiments can include a first and second plurality of barbs having any suitable structural configuration and having a flank disposed at any suitable angle relative to a lengthwise axis of an implantable tissue anchor. In the illustrated embodiment, the gullet 60 is radiused to assist with resisting crack propagation. However, alternative embodiments can include a gullet that is not radiused.

Figure 2:
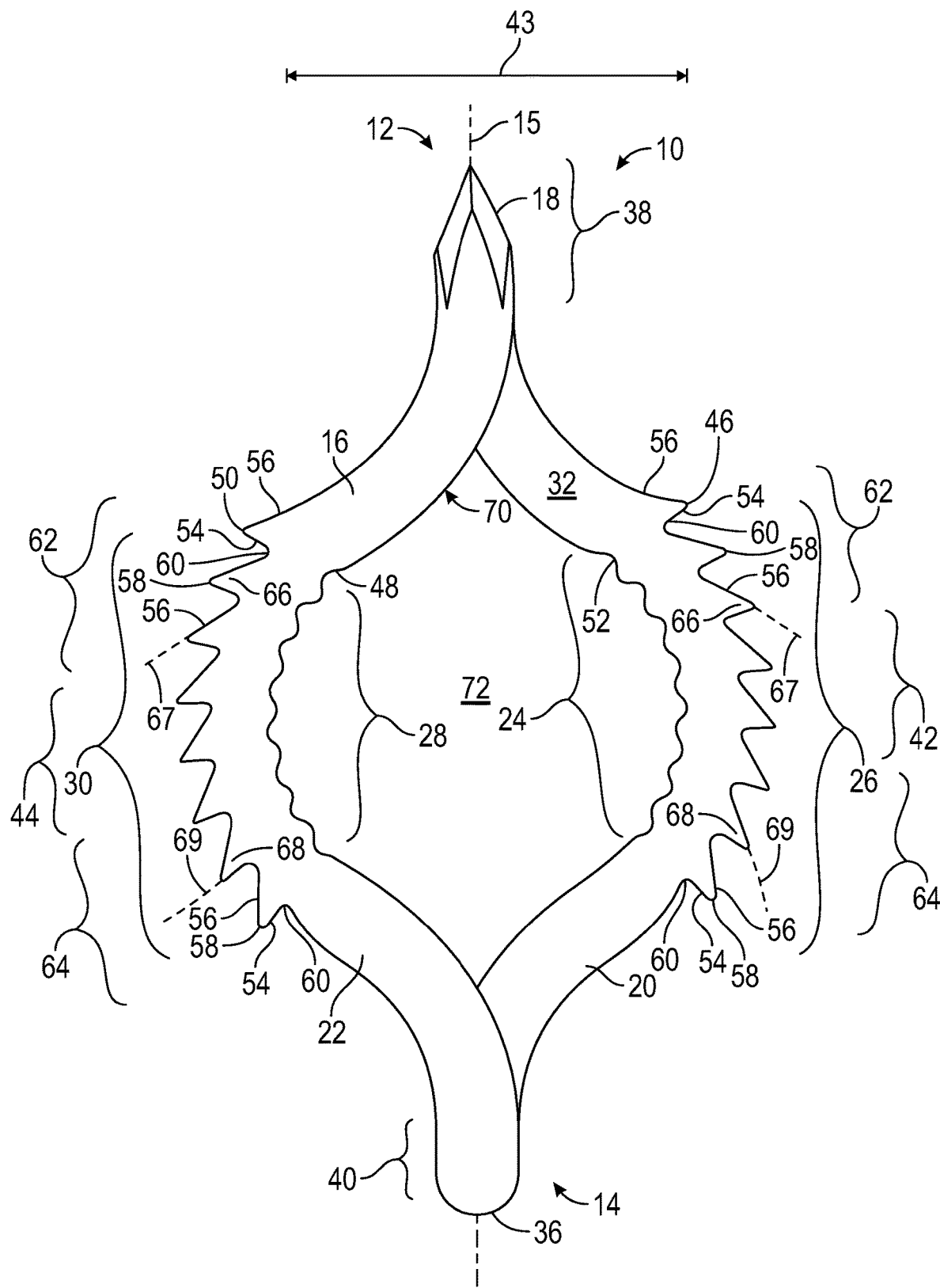
FIG. 2 is a rear view of the tissue anchor illustrated in FIG. 1.

As shown in FIGS. 1 and 2, in the first, expanded configuration the first and second arms 20, 22 define a closed loop 70 and a passageway 72 that extends through the main body 16 of the implantable tissue anchor 10. In the illustrated embodiment, the first and second arms 20, 22 are biased to the first, expanded configuration and define mirrored curved configurations. However, alternative embodiments can include any suitable number of arms positioned in any suitable configuration relative to one another.

A proximal terminus and/or distal terminus included in an implantable tissue anchor can include any structural junction of two portions of a monolithic structure or a connection between two separate members. In the illustrated embodiment, each of the proximal terminus 38 and the distal terminus 40 is a structural junction of two portions of a monolithic structure.

An implantable tissue anchor can have any suitable first length and/or second length and selection of a suitable first length and/or second length of an implantable tissue anchor can be based on various considerations, including the treatment intended to be accomplished using the implantable tissue anchor. Examples of second lengths considered suitable for an implantable tissue anchor include lengths between 5 millimeters and 25 millimeters, lengths between 8 millimeters and 16 millimeters, lengths that are greater than 10 millimeters, lengths that are less than 10 millimeters, lengths about 10 millimeters, and any other length considered suitable for a particular embodiment.

While the implantable tissue anchor 10 has been illustrated as including a cutting tip 18, a first arm 20, a second arm 22, a first plurality of recesses 24, a first plurality of barbs 26, a second plurality of recesses 28, a second plurality of barbs 30, a first planar surface 32, a second planar surface 34, and a blunt tip 36, an implantable tissue anchor can have any suitable structural arrangement and include any suitable number of features, such as those described herein. Selection of a suitable structural arrangement for a tissue anchor and of a suitable number of features to include on a tissue anchor can be based on various considerations, such as the treatment intended to be completed using the implantable tissue anchor. For example, an implantable tissue anchor can include a cutting tip on a first end and/or a second end, any suitable number of barbs and/or recesses, a blunt tip on a first end and/or a second end, and any suitable number and type of surfaces on a first arm and/or second arm. Examples of suitable numbers of barbs and/or recesses to include on an arm of an implantable tissue anchor include at least one, one, two, a plurality, three, four, five, six, seven, eight, nine, ten, more than ten, eleven, twelve, thirteen, fourteen, fifteen, sixteen, seventeen, eighteen, nineteen, twenty, less than eight, more than eight, eight or more, four or more, less than five, less than sixteen, and any other number considered suitable for a particular embodiment. Examples of types of surfaces considered suitable to include on an arm where planar surfaces 32, 34 are illustrated on implantable tissue anchor 10 include planar surfaces, curved surfaces, a first surface that mates with a second surface, and any other surface considered suitable for a particular embodiment.

Figure 7:
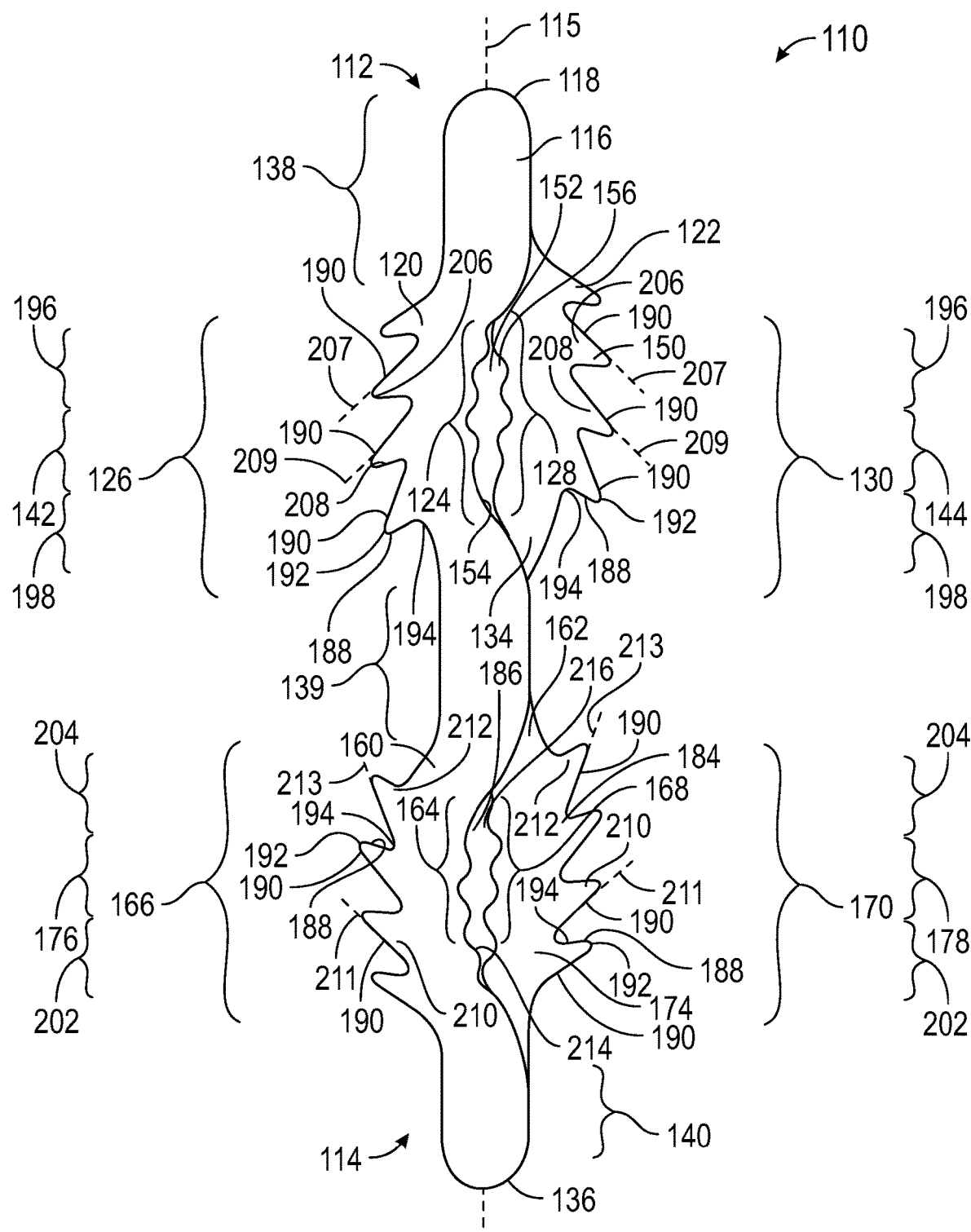
FIG. 7 is a rear view of a second example implantable tissue anchor. The tissue anchor is shown in a first, expanded configuration.

FIGS. 7, 8, 9, 10, and 11 illustrate a second example implantable tissue anchor 110 that is movable between a first, expanded configuration, as shown in FIGS. 7, 8, and 9, and a second, compressed configuration, as shown in FIGS. 10 and 11.

In the illustrated embodiment, the tissue anchor 110 has a first end 112, a second end 114, a lengthwise axis 115, and a main body 116 that defines a blunt tip 118 on the first end 112, a first arm 120, a second arm 122, a first plurality of recesses 124 on the first arm 120, a first plurality of barbs 126 on the first arm 120, a second plurality of recesses 128 on the second arm 122, a second plurality of barbs 130 on the second arm 122, a first planar surface 132 on the first arm 120, a second planar surface 134 on the second arm 122, a blunt tip 136 on the second end 114, a third arm 160, a fourth arm 162, a third plurality of recesses 164 on the third arm 160, a third plurality of barbs 166 on the third arm 160, a fourth plurality of recesses 168 on the fourth arm 162, a fourth plurality of barbs 170 on the fourth arm 162, a third planar surface 172 on the third arm 160, and a fourth planar surface 174 on the fourth arm 162. The main body 116 of the tissue anchor 110 has a first length 117 in the first, expanded configuration and a second length 119 in the second, compressed configuration that is greater than the first length 117. The blunt tip 118 on the first end 112 and the blunt tip 136 of the second end 114 are spherically blunted (e.g., tangent-ogive shaped tips). However, alternative embodiments can include blunted tips that have any suitable structural configuration. The first arm 120 and the second arm 122 terminate in a proximal terminus 138 and an intermediate terminus 139. The first planar surface 132 has a central portion 142 disposed between the first and second ends 112, 114 and the second planar surface 134 has a central portion 144 disposed between the first and second ends 112, 114. The third arm 160 and the fourth arm 162 terminate in the intermediate terminus 139 and a distal terminus 140. The third planar surface 172 has a central portion 176 disposed between the first and second ends 112, 114 and the fourth planar surface 174 has a central portion 178 disposed between the first and second ends 112, 114.

In the first, expanded configuration the first plurality of barbs 126 is free of the second plurality of recesses 128, the second plurality of barbs 130 is free of the first plurality of recesses 124, the central portion 142 of the first planar surface 132 is disposed a first distance 143 from the central portion 144 of the second planar surface 134, the third plurality of barbs 166 is free of the fourth plurality of recesses 168, the fourth plurality of barbs 170 is free of the third plurality of recesses 164, the central portion 176 of the third planar surface 172 is disposed a first distance 177 from the central portion 178 of the fourth planar surface 174.

In the second, compressed configuration each barb of the first plurality of barbs 126 is partially disposed within a distinct recess of the second plurality of recesses 128, each barb of the second plurality of barbs 130 is partially disposed within a distinct recess of the first plurality of recesses 124, the central portion 142 of the first planar surface 132 is disposed a second distance 145 from the central portion 144 of the second planar surface 134, each barb of the third plurality of barbs 166 is partially disposed within a distinct recess of the fourth plurality of recesses 168, each barb of the fourth plurality of barbs 170 is partially disposed within a distinct recess of the third plurality of recesses 164, the central portion 176 of the third planar surface 172 is disposed a second distance 179 from the central portion 178 of the fourth planar surface 174. The second distance 145 is less that the first distance 143 and the second distance 179 is less than the first distance 177. In the illustrated embodiment, in the second, compressed configuration a first barb 146 of the first plurality of barbs 126 is partially disposed within a first recess 148 of the second plurality of recesses 128, a first barb 150 of the second plurality of barbs 130 is partially disposed within a first recess 152 of the first plurality of recesses 124, the first planar surface 132 is disposed adjacent to and contacts the second planar surface 134 (e.g., along the central portions 142, 144), a first barb 180 of the third plurality of barbs 166 is partially disposed within a first recess 182 of the fourth plurality of recesses 168, a first barb 184 of the fourth plurality of barbs 170 is partially disposed within a first recess 186 of the third plurality of recesses 164, and the third planar surface 172 is disposed adjacent to and contacts the fourth planar surface 174 (e.g., along the central portions 176, 178).

In the illustrated embodiment, in the second, compressed configuration the recesses of the first plurality of recesses 124 are staggered relative to the recesses of the second plurality of recesses 128 along the lengthwise axis 115, the barbs of the first plurality of barbs 126 are staggered relative to the barbs of the second plurality of barbs 130 along the lengthwise axis 115, the recesses of the third plurality of recesses 164 are staggered relative to the recesses of the fourth plurality of recesses 168 along the lengthwise axis 115, and the barbs of the third plurality of barbs 166 are staggered relative to the barbs of the fourth plurality of barbs 170 along the lengthwise axis 115. This structural arrangement allows the implantable tissue anchor 110 to have a cross-sectional area taken along a plane that is perpendicular to the lengthwise axis 115 that is constant along the length of an arm of the plurality of arms 120, 122, 160, 162 avoiding any neck-downed portions, which can impart weakness into the implantable tissue anchor 110.

Each barb of the first plurality of barbs 126, the second plurality of barbs 130, the third plurality of barbs 166, and the fourth plurality of barbs 170 has a face 188, a flank 190, a tip 192, and a gullet 194. In the first, expanded configuration the face 188 of a first set 196 of the first and second plurality of barbs 126, 130 is directed away from the first end 112 of the implantable tissue anchor 110 and the face 188 of a second set 198 of the first and second plurality of barbs 126, 120 is directed toward the second end 114 of the implantable tissue anchor 110. In addition, in the first, expanded configuration the face 188 of a first set 202 of the third and fourth plurality of barbs 166, 170 is directed away from the second end 114 of the implantable tissue anchor 110 and the face 188 of a second set 204 of the third and fourth plurality of barbs 166, 170 is directed toward the first end 112 of the implantable tissue anchor 110.

In the first, expanded configuration the flank 190 of a first barb 206 of each of the first and second plurality of barbs 126, 130 is disposed at a first angle 207 relative to the lengthwise axis 115 of the implantable tissue anchor 110 and the flank 190 of a second barb 208 of each of the first and second plurality of barbs 126, 130 is disposed at a second angle 209 relative to the lengthwise axis 115 of the implantable tissue anchor 110. The first angle 207 is greater than 90 degrees and the second angle 209 is greater than the first angle 207 (e.g., greater than 135 degrees). In addition, in the first, expanded configuration the flank 190 of a first barb 210 of each of the third and fourth plurality of barbs 166, 170 is disposed at a first angle 211 relative to the lengthwise axis 115 of the implantable tissue anchor 110 and the flank 190 of a second barb 212 of each of the third and fourth plurality of barbs 166, 170 is disposed at a second angle 213 relative to the lengthwise axis 115 of the implantable tissue anchor 110. The first angle 211 is greater than 90 degrees and the second angle 213 is greater than the first angle 211 (e.g., greater than 135 degrees). However, alternative embodiments can include a first plurality of barbs, a second plurality of barbs, a third plurality of barbs, and a fourth plurality of barbs having any suitable structural configuration and having a flank disposed at any suitable angle relative to a lengthwise axis of an implantable tissue anchor.

As shown in FIG. 7, in the first, expanded configuration the first and second arms 120, 122 define a first closed loop 154 and a first passageway 156 and the third and fourth arms 160, 162 define a second closed loop 214 and a second passageway 216. Each of the first passageway 156 and the second passageway 216 extends through the main body 116 of the implantable tissue anchor 110. In the illustrated embodiment, the first, second, third, and fourth arms 130, 132, 160, 162 are biased to the first, expanded configuration and define mirrored sinusoidal configurations.

An implantable tissue anchor can include any structural junction of two portions of a monolithic structure or a connection between two separate members. For example, a first arm, a second arm, a third arm, and a fourth arm can be formed as a monolithic structure. Alternatively, a first arm and a second arm can be formed as a first monolithic structure and a third arm and a fourth arm can be formed as a second monolithic structure attached to the first monolithic structure or a first arm and a fourth arm can be formed as a first monolithic structure and a second arm and a third arm can be formed as a second monolithic structure attached to the first monolithic structure.

A barb and recess included in an implantable tissue anchor can have any suitable structural arrangement and selection of a suitable structural arrangement for a barb and/or recess can be based on various considerations, including the type of tissue within which the implantable tissue anchor is intended to be deployed. In the illustrated embodiment, each barb has a sharp tip and each recess has a configuration that receives and mates with a barb. However, in alternative embodiments, the tip of a barb, or each barb, can be radiused such that any sharp edges are removed and a recess, or each recess, can be configured to receive and mate with the barb.

An implantable tissue anchor can be formed of any suitable material and using any suitable technique or method of manufacture. Selection of a suitable material to form an implantable tissue anchor and of a suitable technique or method to manufacture an implantable tissue anchor can be based on various considerations, including the intended use of the tissue anchor. Examples of materials considered suitable to form an implantable tissue anchor include biocompatible materials, materials that can be made biocompatible, metals, alloys, Nitinol, synthetic materials, polymers, polypropylene, polyurethane, biocompatible high-density polyethylene, natural materials, a single material, and any other material considered suitable for a particular embodiment. Examples of techniques and methods of manufacture considered suitable to form an implantable tissue anchor include injection molding, injection molding in a first, expanded configuration to impart bias to the tissue anchor, overmolding, insert molding, additive manufacturing, such as additive manufacturing that constructs an implantable tissue anchor from layering materials, manufacturing an implantable tissue anchor using any suitable technique or method in a first, expanded configuration to impart bias to the tissue anchor, and any other technique or method considered suitable for a particular embodiment. For example, an implantable tissue anchor can be formed using an overmolding process in which a first material (e.g., Nitinol) forms a first portion of an implantable tissue anchor (e.g., main body without barbs and/or recesses) and a second material (e.g., polymer), which is overmolded over the first material, forms a second portion of the implantable tissue anchor (e.g., barbs and/or recesses).

An implantable tissue anchor can be entirely, or partially, coated with a medicament for localized drug elution, an echogenic material, a fluoroscopic material, a magnetic resonance imaging (MRI) compatible material, can be formed entirely of an echogenic material, and/or include one or more echogenic features, to aid in visualization (e.g., sonographic) during implantation. An echogenic material included in an implantable tissue anchor can include those that are compatible with and can be visualized using magnetic resonance imaging (MRI) or other imaging modalities (e.g., visible under sonography). For example, a first end, a second end, a proximal terminus, an intermediate terminus, a distal terminus, a barb, a recess, a plurality of barbs, a plurality of recesses, a portion disposed adjacent to a plurality of barbs, and any other feature included in an implantable tissue anchor can include an echogenic material (e.g., MRI compatible material). Echogenic materials can be applied to an implantable tissue anchor using any suitable method or technique. For example, echogenic materials can be applied, adhered, or fused to the material forming an implantable tissue anchor (e.g., to create one or more marker bands). Alternatively, an echogenic material can be added as a filler into the material being used to form an implantable tissue anchor prior to forming the implantable tissue anchor.

Various methods of treatment using an implantable tissue anchor are described herein. While the methods described herein are shown and described as a series of acts, it is to be understood and appreciated that the methods are not limited by the order of acts, as some acts may in accordance with these methods may be omitted, occur in the order shown and/or described, occur in different orders, and/or occur concurrently with other acts described herein.

Figure 12:
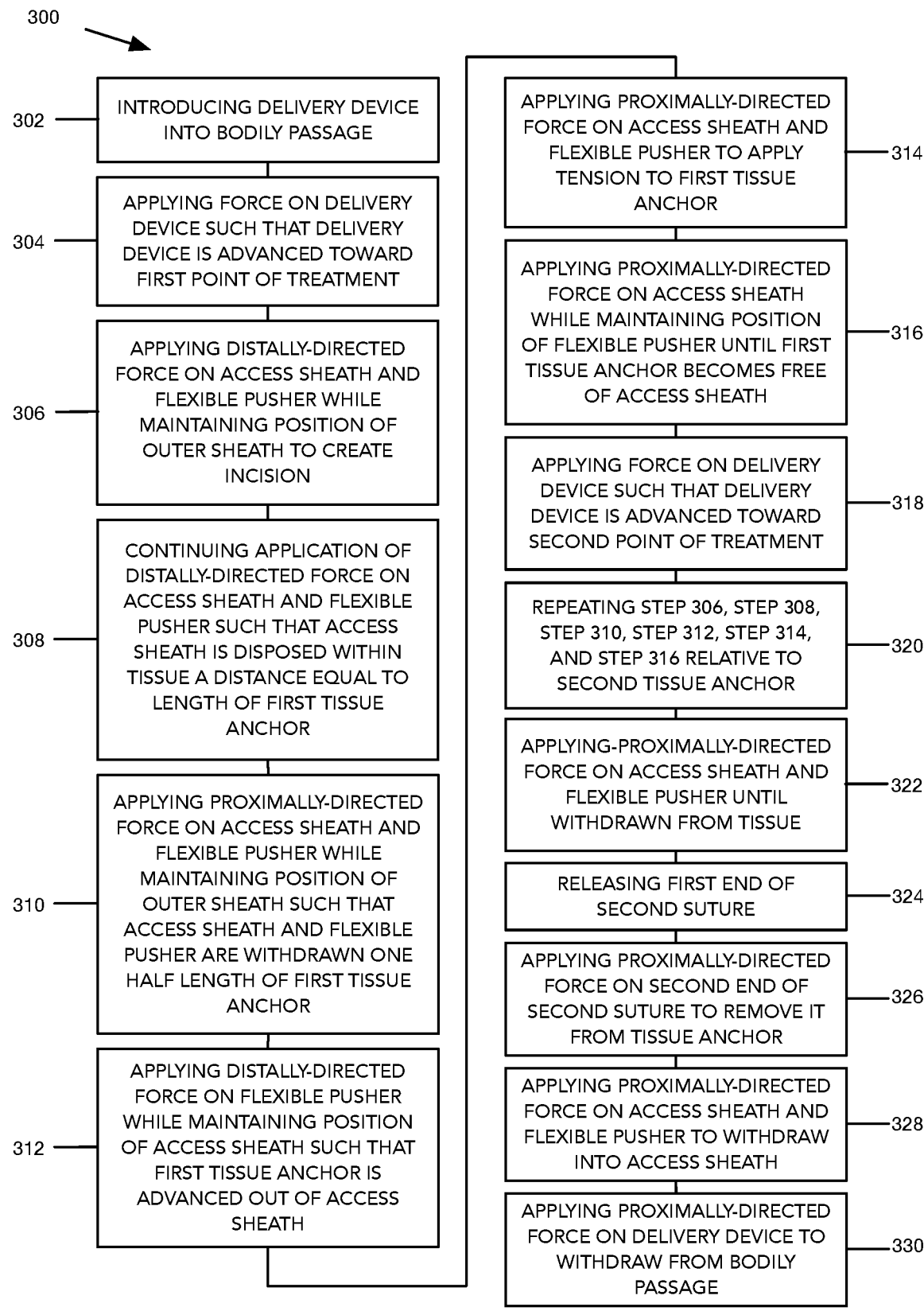
FIG. 12 is a schematic illustration of an example method of adjusting tissue within the body.

FIG. 12 illustrates a schematic illustration of an example method 300 of adjusting tissue within a body using an implantable tissue anchor. The methods described herein can be accomplished within any suitable body, such as the body of an animal (e.g., a human).

An initial step 302 comprises introducing a delivery device into a bodily passage. The delivery device includes an outer sheath, an access sheath partially disposed within the outer sheath, a flexible pusher partially disposed within the access sheath, first and second implantable tissue anchors disposed distal to the flexible pusher and within the access sheath, a first suture attaching the first and second implantable tissue anchors to one another, and a second suture attached to the second implantable tissue anchor and disposed through the flexible pusher. The access sheath has a distal portion that has a first, substantially straight configuration when disposed within the outer sheath and a second, curved configuration when free of the outer sheath. Each of the first and second implantable tissue anchors is in the second, compressed configuration. Another step 304 comprises applying a force on the delivery device such that the delivery device is advanced toward a first point of treatment. Another step 306 comprises applying a distally-directed force on the access sheath and the flexible pusher while maintaining the position of the outer sheath such that the access sheath is advanced distally relative to the outer sheath and creates an incision in the tissue defining the bodily passage. Another step 308 comprises continuing the application of the distally-directed force on the access sheath and the flexible pusher such that the access sheath advances into the tissue a distance equal to the length of the first implantable tissue anchor. Another step 310 comprises applying a proximally-directed force on the access sheath and flexile pusher while maintaining the position of the outer sheath such that the access sheath and flexible pusher are withdrawn into the outer sheath and from the tissue a distance equal to about ½ the length of the first implantable tissue anchor. Another step 312 comprises applying a distally-directed force on the flexible pusher while maintaining the position of the access sheath such that the first tissue anchor advances out of the access sheath and into the tissue a distance equal to about ½ the length of the first tissue anchor. Another step 314 comprises applying a proximally-directed force on the access sheath and the flexible pusher such that the access sheath and the flexible pusher are partially withdrawn from the tissue and tension is applied to the first tissue anchor via the first and second sutures. Another step 316 comprises applying a proximally-directed force on the access sheath while maintaining the position of the flexible pusher until the first tissue anchor becomes free of the access sheath and is disposed within the tissue in the first, expanded configuration. Another step 318 comprises applying a force on the delivery device such that the delivery device is advanced toward a second point of treatment. Another step 320 comprises repeating step 306, step 308, step 310, step 312, step 314, and step 316 relative to the second tissue anchor. Another step 322 comprises applying a proximally-directed force on the access sheath and the flexible pusher such that the access sheath and the flexible pusher are withdrawn from the tissue defining the bodily passage. Another step 324 comprises releasing a first end of the second suture from attachment to the second implantable tissue anchor. Another step 326 comprises applying a proximally-directed force on the second end of the second suture such that it becomes free of attachment to the second implantable tissue anchor. Another step 328 comprises applying a proximally-directed force on the access sheath and the flexible pusher while maintaining the position of the outer sheath such that the access sheath and the flexible pusher are withdrawn into the outer sheath. Another step 330 comprises applying a proximally-directed force on the delivery device such that the outer sheath, access sheath, flexible pusher, and suture are withdrawn from the bodily passage.

Step 302 can be accomplished by introducing a delivery device into any suitable bodily passage and selection of a suitable bodily passage to introduce a delivery device can be based on various considerations, including the treatment intended to be performed. Examples of bodily passages considered suitable to introduce a delivery device include the urethra, an airway, and any other bodily passage considered suitable for a particular embodiment.

Figure 13:
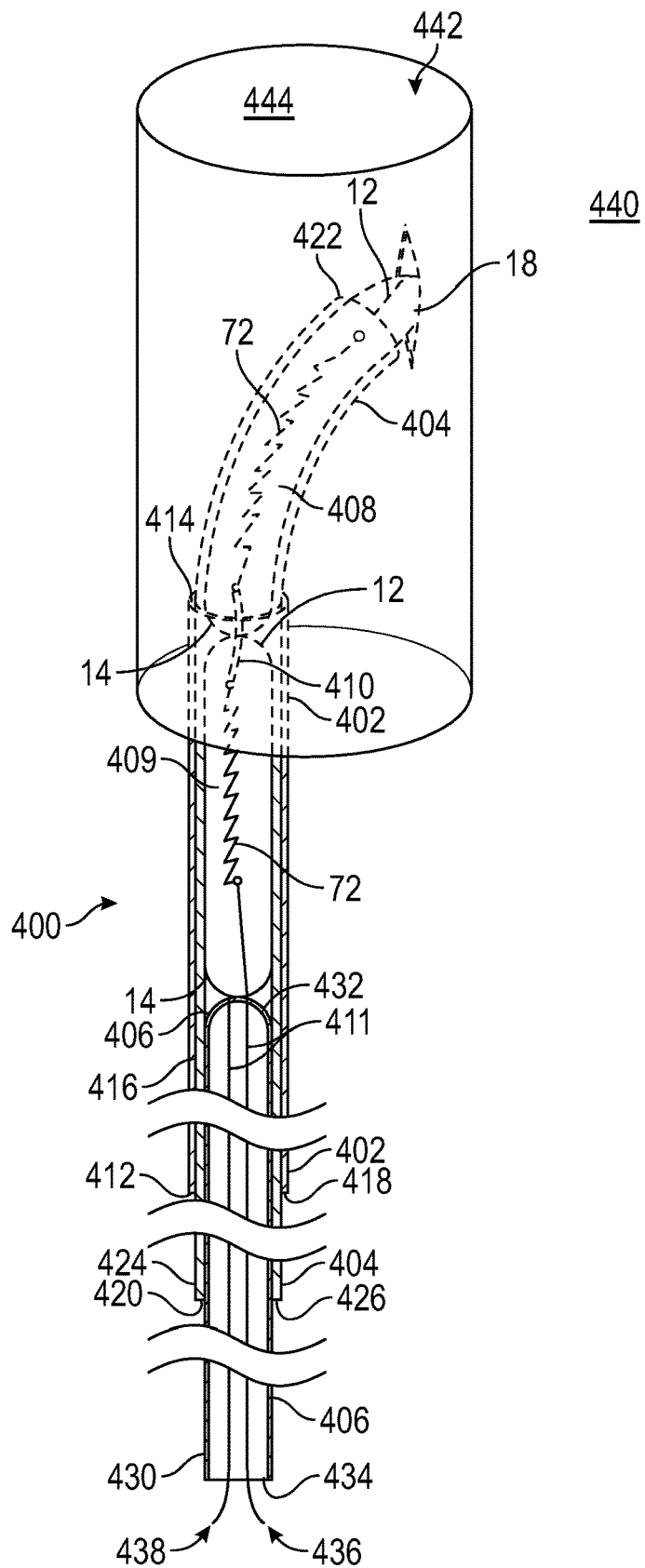
FIG. 13 is a partial perspective view of a delivery device disposed within a bodily passage. The access sheath is partially disposed distal to the outer sheath and each of the first and second implantable tissue anchors is in the second, compressed configuration.

Step 302 can be accomplished using any suitable delivery device capable of deploying an implantable tissue anchor. An example delivery device 400 is shown in FIG. 13. The delivery device 400 includes an outer sheath 402, an access sheath 404 partially disposed within the outer sheath 402, a flexible pusher 406 partially disposed within the access sheath 404, a first implantable tissue anchor 408 and a second implantable tissue anchor 409 disposed distal to the flexible pusher 406 and within the access sheath 404, a first suture 410 connecting the first and second implantable tissue anchors 408, 409, and a second suture 411 attached to the second implantable tissue anchor 409 and disposed through the flexible pusher 406. The outer sheath 402 has a proximal end 412, a distal end 414, and a main body 416 that defines a lumen 418 that extends from the proximal end 412 to the distal end 414. The access sheath 404 has a proximal end 420, a distal end 422, and a main body 424 that defines a lumen 426 and a distal portion 428. The lumen 426 of the access sheath 404 extends from the proximal end 420 to the distal end 422. The distal portion 428 has first, substantially straight configuration when disposed within the outer sheath 402 and a second, curved configuration, as shown in FIGS. 13, 14, 15, and 16, when free of the outer sheath 402. In the curved configuration, the distal portion 428 can be defined at any suitable angle relative to a proximal portion of the access sheath 404 that extends proximal to the distal portion 428. Angles considered suitable to position a distal portion of an access sheath relative to a proximal portion include angles between 0 degree and 180 degrees, between 20 degrees and 145 degrees, between 30 degrees and 135 degrees, between 90 degrees and 180 degrees, angles less than 90 degrees, angles about 90 degrees, angles greater than 90 degrees, angles greater than 180 degrees, and any other angle considered suitable for a particular embodiment. The flexible pusher 406 has a proximal end 430, a distal end 432, and a lumen 434 that extends from the proximal end 430 to the distal end 432. An outer sheath, access sheath, flexible pusher, and a suture included in a method of adjusting tissue within the body can be formed of any suitable material and manufactured using any suitable technique or method, such as conventional materials, the materials described herein, and conventional manufacturing techniques and methods. For example, an access sheath can be formed of a shape-memory alloy (e.g., Nitinol).

Figure 14:
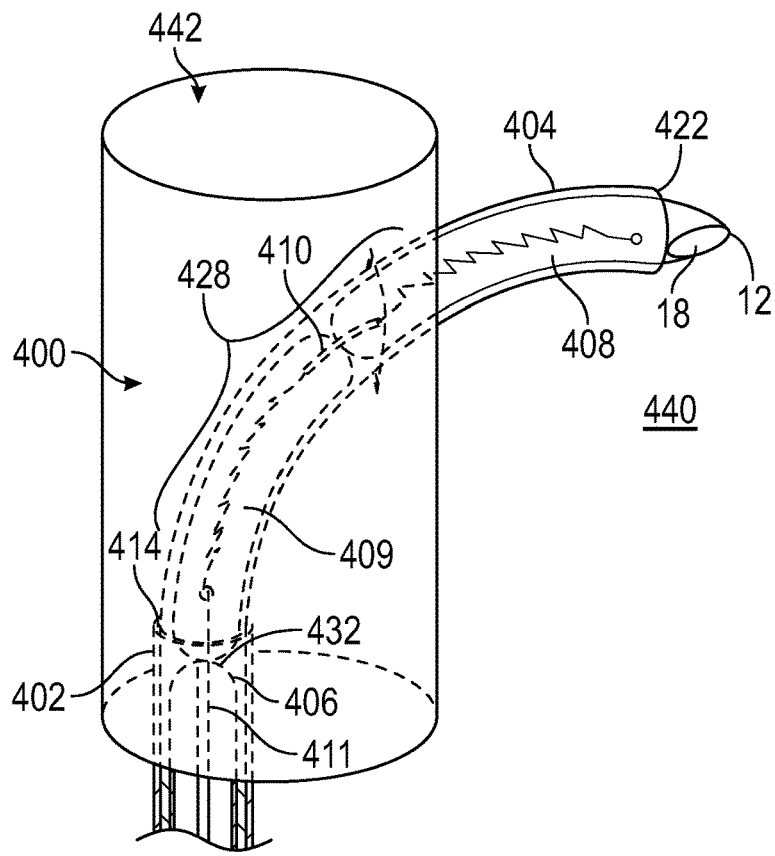
FIG. 14 is a partial perspective view of a delivery device disposed within a bodily passage and partially disposed within tissue. The access sheath is partially disposed within the tissue and each of the implantable tissue anchors is in the second, compressed configuration.

Step 302 can be accomplished using any suitable implantable tissue anchors and selection of suitable implantable tissue anchors to utilize in a method of adjusting tissue in a body can be based on various considerations, such as the treatment intended to be performed. Examples of implantable tissue anchors considered suitable to utilize in a method of adjusting tissue in a body include implantable tissue anchor 10, implantable tissue anchor 110, variations of the implantable tissue anchors described herein, and any other implantable tissue anchor considered suitable for a particular embodiment. In the illustrated embodiment, each of the first and second implantable tissue anchors 408, 409 are similar to implantable tissue anchor 10 and are being deployed within tissue 440. As shown in FIGS. 13 and 14, the first end 12 of the first implantable tissue anchor 408 is disposed distal to the access sheath 404 such that the cutting tip 18 can be used to assist with creating an incision into the tissue defining the wall of the bodily passage within which the delivery device has been introduced and to assist with creating an access path for the delivery device and the first implantable tissue anchor. In alternative embodiments, an implantable tissue anchor can be entirely disposed within an access sheath that includes a sharp distal tip, which can be used to create an incision into the tissue defining the wall of the bodily passage within which a delivery device has been introduced and to assist with creating an access path for a delivery device and implantable tissue anchor.

As shown in FIG. 13, the second end 14 of the first implantable tissue anchor 408 is disposed adjacent to the first end 12 of the second implantable tissue anchor 408 and the second end 14 of the second implantable tissue anchor 409 is disposed adjacent to the distal end 432 of the flexible pusher 406 and within the access sheath 404. The first suture 410 is disposed through the passageways 72 defined by each of the first and second implantable tissue anchors 408, 409 such that they are attached to one another. The second suture 411 has a first end 436 and a second end 438. As shown in FIG. 13, the each of the first and second ends 436, 438 of the second suture 411 are disposed proximal to the proximal end 430 of the flexible pusher 406 and the second suture 411 extends through the passageway 72 defined by the second implantable tissue anchor 409 and the lumen 434 defined by the flexible pusher 406. In alternative embodiments, a suture can be attached to any suitable portion of a delivery device, such as a flexible pusher, and released from attachment to the portion of the delivery device when the first and second implantable tissue anchors are ready for deployment, or can extend in a lumen defined by the access sheath such that the suture is disposed between an inner wall of the access sheath and the flexible pusher. Alternative embodiments can also include a handle attached to the proximal end of an outer sheath, the proximal end of an access sheath, and/or the proximal end of a flexible member to achieve movement of these components as described herein.

Step 304 can be accomplished by applying any suitable force on any suitable portion of the delivery device such that the delivery device is advanced toward a first point of treatment. For example, a proximal force, a distal force, and/or torque can be applied to the outer sheath 402, or other portions of the delivery device, such that the entire delivery device is advanced toward a point of treatment. A point of treatment can include any portion, or part, of a body of which it is desired to perform treatment. For example, a point of treatment can include the tissue surrounding a stricture defined within the bodily passage (e.g., urethra) within which the delivery device is positioned, muscular tissue adjacent to a lumen, or an organ such that deployment of an implantable tissue anchor biases the organ to a therapeutic position.

Step 306 is accomplished such that the distal portion of the access sheath defines the second, curved configuration. An incision can be made into any suitable tissue and at any suitable location relative to a point of treatment (e.g., a stricture within the bodily passage). For example, an incision can be made into the urethra or the soft palate and at a point of treatment, proximal to a point of treatment, or distal to a point of treatment, depending on the desired treatment intended to be performed. In addition, step 306 is accomplished such that the flexible pusher and implantable tissue anchors are advanced concurrently with the access sheath. FIG. 13 shows the access sheath 404 advanced distally relative to the outer sheath 402 and the first implantable tissue anchor 408 creating an incision in the tissue 440 defining the bodily passage 442 since the implantable tissue anchor 408 is partially disposed distal to the distal end 422 of the access sheath 404. In the illustrated embodiment, the tissue 440 defines the urethra 444. In embodiments in which a first implantable tissue anchor is entirely disposed within an access sheath, the access sheath can define a sharp distal tip that can create an incision (e.g., to complete step 306) and/or path through which a portion of the delivery device can pass (e.g., to complete step 308). In these alternative embodiments, the sharp distal tip of the access sheath can include any suitable structural arrangement, such as a bevel oriented at an angle (e.g., 30 degrees) relative to a lengthwise axis of the access sheath.

Step 308 can be accomplished by advancing the delivery device into any suitable tissue, such as the tissue defining the bodily passage, tissue disposed adjacent to the tissue defining the bodily passage, tissue defining the bodily passage and tissue disposed adjacent to the tissue defining the bodily passage, urethra, the prostate, the soft palate, muscular tissue, an organ, and any other tissue considered suitable for a particular treatment. Optionally, step 308 can be accomplished using any suitable technique or method of visualizing the position of the access sheath relative to the tissue defining the bodily passage, such as sonography, and any other technique or method considered suitable for a particular embodiment. Step 308 is accomplished such that the flexible pusher and implantable tissue anchor are advanced concurrently with the access sheath. FIG. 14 shows the access sheath advanced into the tissue. Optionally, step 308 be accomplished while maintaining the position of the outer sheath. While step 308 has been described as being completed such that the access sheath advances into the tissue a distance equal to the length of the first implantable tissue anchor, an access sheath can be advanced any suitable distance into tissue. Selection of a suitable distance can be based on various considerations, including the location of a desired deployment site. Examples of distances considered suitable to advance an access sheath into tissue include distances equal to the length of a first implantable tissue anchor, distances equal to about the length of a first implantable tissue anchor, distances that are less than the length of a first implantable tissue anchor, distances that are greater than the length of a first implantable tissue anchor, distances equal to about ½ the length of a first implantable tissue anchor, and any other distance considered suitable for a particular embodiment.

Step 310 can optionally be accomplished using any suitable technique or method of visualizing the position of the access sheath relative to the tissue defining the bodily passage, such as sonography, and any other technique or method considered suitable for a particular embodiment. While step 310 has been described as being completed such that the access sheath is withdrawn into the outer sheath and from the tissue a distance equal to ½ the length of the first implantable tissue anchor, an access sheath can be withdrawn any suitable distance from the tissue. Selection of a suitable distance can be based on various considerations, including the location of a desired deployment site. Examples of distances considered suitable to withdraw an access sheath from tissue include distances equal to ½ the length of a first implantable tissue anchor, distances equal to about ½ the length of a first implantable tissue anchor, distances that are less than ½ the length of a first implantable tissue anchor, distances that are greater than ½ the length of a first implantable tissue anchor, and any other distance considered suitable for a particular embodiment.

Figure 15:
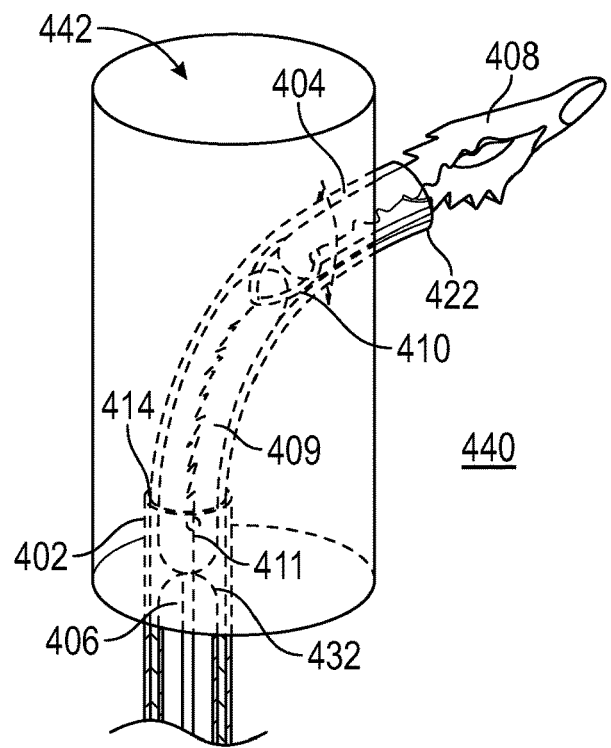
FIG. 15 is a partial perspective view of a delivery device disposed within a bodily passage and partially disposed within tissue. The access sheath is partially disposed within the tissue and the first implantable tissue anchor is partially in the first, expanded configuration.

Step 312 can optionally be accomplished using any suitable technique or method of visualizing the position of an implantable tissue anchor relative to the access sheath and/or tissue defining the bodily passage, such as sonography, and any other technique or method considered suitable for a particular embodiment. FIG. 15 shows ½ of the first implantable tissue anchor 408 disposed within the tissue 440 such that the first implantable tissue anchor 408 is partially disposed in the first, expanded configuration (e.g., a second end portion of the tissue anchor is in the second compressed configuration and a first end portion is in the first, expanded configuration). While step 312 has been described as being completed such that the first implantable tissue anchor is advanced out of the access sheath and into the tissue a distance equal to ½ the length of the first implantable tissue anchor, an implantable tissue anchor can be advanced any suitable distance into the tissue. Selection of a suitable distance can be based on various considerations, including the location of a desired deployment site. Examples of distances considered suitable to advance an implantable tissue anchor into tissue include distances equal to ½ the length of an implantable tissue anchor, distances equal to about ½ the length of an implantable tissue anchor, distances that are less than ½ the length of an implantable tissue anchor, distances that are greater than ½ the length of an implantable tissue anchor, and any other distance considered suitable for a particular embodiment. In an alternative embodiment, step 310 and step 312 can be omitted and an alternative step comprising applying a proximally-directed force on the access sheath while maintaining the position of the outer sheath and flexible pusher such that the access sheath is withdrawn into the outer sheath and from the tissue a distance equal to about ½ the length of the implantable tissue anchor can be completed.

Step 314 provides a mechanism for allowing the first and second plurality of barbs 26, 30 to puncture the tissue 440 and become embedded within the tissue 440. In addition, step 314 provides a mechanism for expanding the tissue between the first and second arms such that the tissue at the point of treatment becomes compressed and widens the bodily passage (e.g., foreshortening compresses walls of the tissue within which it is deployed). Optionally, step 314 be accomplished while maintaining the position of the outer sheath and/or can be accomplished by applying a proximally-directed force on the second suture (e.g., first and second ends 436, 438 of the second suture 411).

Figure 16:
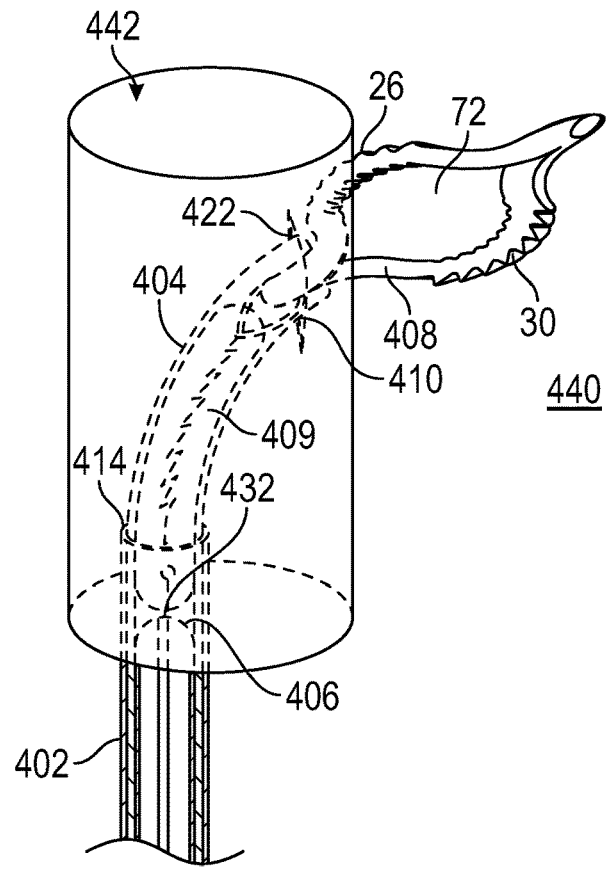
FIG. 16 is a partial perspective view of a delivery device disposed within a bodily passage and partially disposed within tissue. The access sheath is partially disposed within the tissue and the first implantable tissue anchor is partially in the first, expanded configuration.

Step 316 is accomplished such that the entire first implantable tissue anchor is disposed in the first, expanded configuration and the flexible pusher and access sheath are disposed within the bodily passage. Alternatively, step 316 can comprise: applying a proximally-directed force on the access sheath while maintaining the position of the flexible pusher until the first implantable tissue anchor is mostly free of the access sheath and is disposed within the tissue, repeating step 314, and then applying a proximally-directed force on the access sheath while maintaining the position of the flexible pusher until the first implantable tissue anchor becomes free of the access sheath and is disposed within the tissue. FIG. 16 shows the access sheath 404 being withdrawn from the tissue 440 and exposing the first implantable tissue anchor 408.

Figure 17:
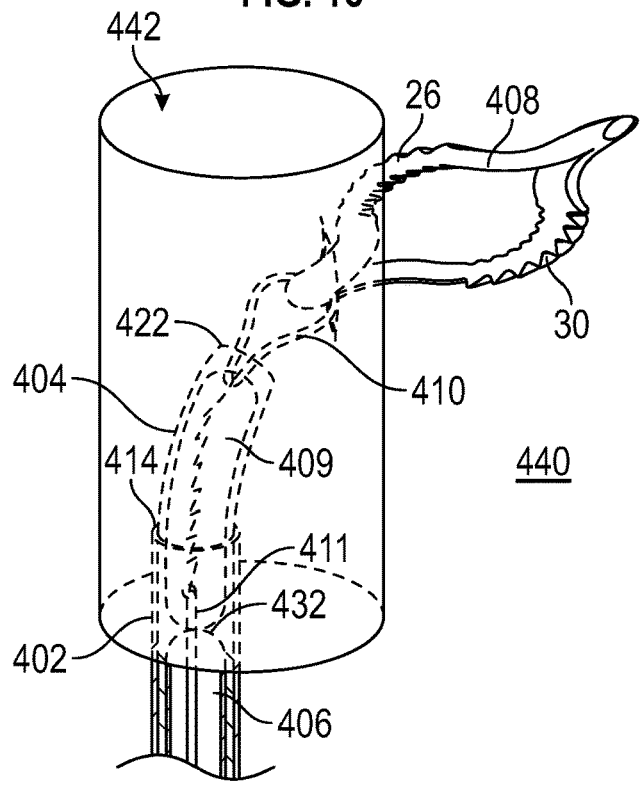
FIG. 17 is a partial perspective view of a delivery device disposed within a bodily passage and partially disposed within tissue. The first implantable tissue anchor is in the first, expanded configuration.

An optional step that can be completed subsequent to step 316 comprises applying a proximally-directed force on the access sheath and flexible pusher and/or on the second suture (e.g., first and second ends 436, 438 of the second suture 411). This optional step provides a mechanism for allowing the first and second plurality of barbs 26, 30 to become embedded within the tissue 440. FIG. 17 shows the access sheath 404 withdrawn from the tissue 440 and a portion of the first implantable tissue anchor 408 disposed within the bodily passage 442. When implanted, the barbs of the first implantable tissue anchors described herein are disposed at an angle (e.g., 90 degrees, substantially 90 degrees) relative to the surface that has been cut or disturbed for placement of the implantable tissue anchor. Furthermore, since the implantable tissue anchors described herein are biased to the first, expanded configuration, when deployed the barbs are forced into the tissue to increase fixation of the implantable tissue anchor within the tissue.

An optional step that can be completed subsequent to step 316 includes evaluating the placement of the first implantable tissue anchor. This optional step can optionally be accomplished using any suitable technique or method of visualizing the position of the first implantable tissue anchor relative to the tissue defining the bodily passage, such as sonography, and any other technique or method considered suitable for a particular embodiment. If the placement of the first implantable tissue anchor is not desired, additional optional steps that can be completed comprise: applying a distally-directed force on the access sheath while maintaining the position of the outer sheath such that the access sheath is advanced over the first implantable tissue anchor (e.g., partially, or entirely); applying a force on the access sheath to a desired location within the tissue; and repeating step 306, step 308, step 310, step 312, step 314, step 316, and/or the optional step of evaluating the placement of the implantable tissue anchor.

Step 318 can be accomplished by applying any suitable force on any suitable portion of the delivery device such that the delivery device is advanced toward a second point of treatment. For example, a proximal force, a distal force, and/or torque can be applied to the outer sheath 402, or other portions of the delivery device, such that the delivery device is advanced toward a second point of treatment. A second point of treatment can include any portion, or part, of a body of which it is desired to perform treatment and can be positioned proximal to the first point of treatment, distal to the first point of treatment, and/or circumferentially adjacent to the first point of treatment on a plane disposed at an angle to (e.g., orthogonally) a lengthwise axis of the bodily passage.

Step 320 can be accomplished by repeating each of step 306, step 308, step 310, step 312, step 314, and step 316 relative to the second tissue anchor 409.

Figure 18:
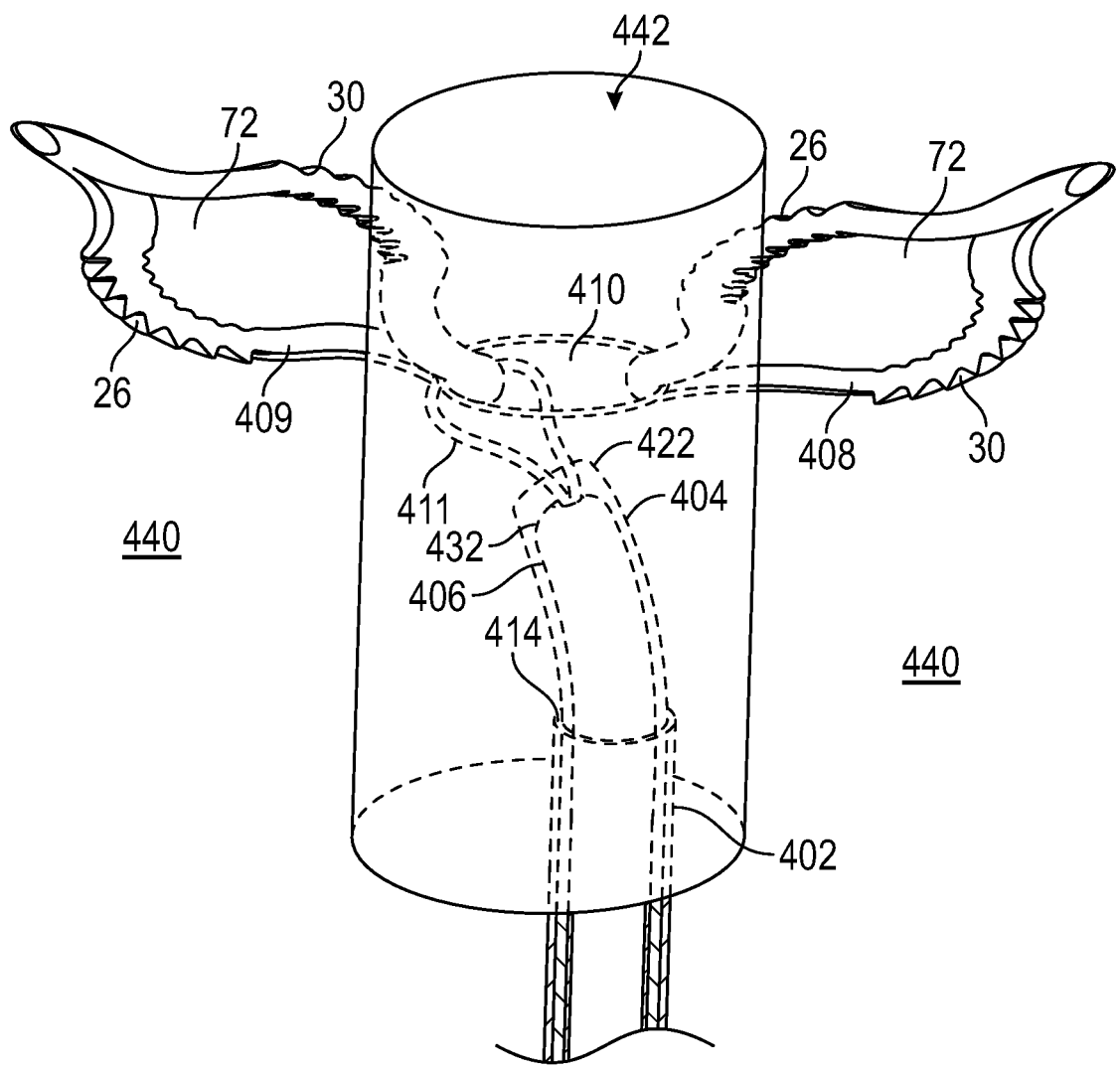
FIG. 18 is a partial perspective view of a delivery device disposed within a bodily passage and partially disposed within tissue. The second implantable tissue anchor is in the first, expanded configuration.

Step 322 is accomplished such that the entire second implantable tissue anchor is disposed in the first, expanded configuration and the flexible pusher and access sheath are disposed within the bodily passage. Alternatively, step 322 can comprise: applying a proximally-directed force on the access sheath while maintaining the position of the flexible pusher until the second implantable tissue anchor is mostly free of the access sheath and is disposed within the tissue, repeating step 314, and then applying a proximally-directed force on the access sheath while maintaining the position of the flexible pusher until the second implantable tissue anchor becomes free of the access sheath and is disposed within the tissue. FIG. 18 shows the access sheath 404 withdrawn from the tissue 440 and exposing the second implantable tissue anchor 409, which is disposed circumferentially adjacent to the first implantable tissue anchor 408.

Step 324 can be accomplished by releasing any force being applied on the first end of the second suture, or any portion of the second suture disposed between the first end and the implantable tissue anchor. For example, a user's hand can be used to apply a force on each of the first and second ends of the second suture during step 302, step 304, step 306, step 308, step 310, step 312, step 314, step 316, step 318, step 320, and/or step 322 to maintain its attachment to the second implantable tissue anchor.

Step 326 can be accomplished by applying a proximally directed force on the second end of the second suture, or any portion of the second suture disposed between the second end and the second implantable tissue anchor until the second suture is withdrawn from the passageway 72 and/or the bodily passage. In an alternative embodiment, a delivery device can omit the inclusion of a second suture and omit step 324 and step 326. Alternatively, an implantable tissue anchor can be attached to a flexible pusher using any other technique or method considered suitable. For example, a clamp or other structure can be used to releasably attach an implantable tissue anchor to a flexible pusher. The clamp can be moved between closed and open configurations to introduce and deploy the implantable tissue anchor as described herein.

Step 328 provides a mechanism for positioning the access sheath in the first, straight configuration and preventing the access sheath and flexible pusher from damaging tissue as the delivery device is withdrawn from the bodily passage in step 330.

Step 330 can be accomplished by applying a proximally directed force on any suitable portion of the delivery device to withdraw the outer sheath, access sheath, flexible pusher, and suture from the bodily passage.

Any of the steps described in method 300 can be repeated any suitable number of times. For example, in treatments in which it is desired to deploy multiple implantable tissue anchors, method 300 can be repeated with third and fourth implantable tissue anchors. Utilizing the implantable tissue anchors and the methods described herein are considered advantageous at least because they do not require full perforation between an interior surface and exterior surface (e.g., first and second walls of a portion of a body (e.g., vessel, prostate)) to implant the tissue anchors (e.g., the implantable tissue anchors can be deployed within tissue having any thickness), the tissue anchors can be deployed to treat any suitable bodily passage, the tissue anchors can be deployed at any suitable angle within the tissue, and the bias of the tissue anchors can be utilized to compress the tissue and address any narrowing of bodily passages adjacent to where the tissue anchors have been deployed (e.g., reduce or eliminate stricture within bodily passage). In addition, the implantable tissue anchors provide a mechanism for treating various conditions, such as OSA, benign prostatic hyperplasia, and any other condition considered suitable for a particular embodiment.

While the first and second implantable tissue anchors 408, 409 have been illustrated as being partially disposed within the bodily passage 442 after deployment, as shown in FIG. 18, a tissue anchor can be deployed such that any suitable portion of the tissue anchor is disposed within the bodily passage or tissue. For example, in alternative embodiments, one of a first tissue anchor and a second tissue anchor, or both first and second tissue anchors, can be entirely disposed within tissue.

Figure 19A:
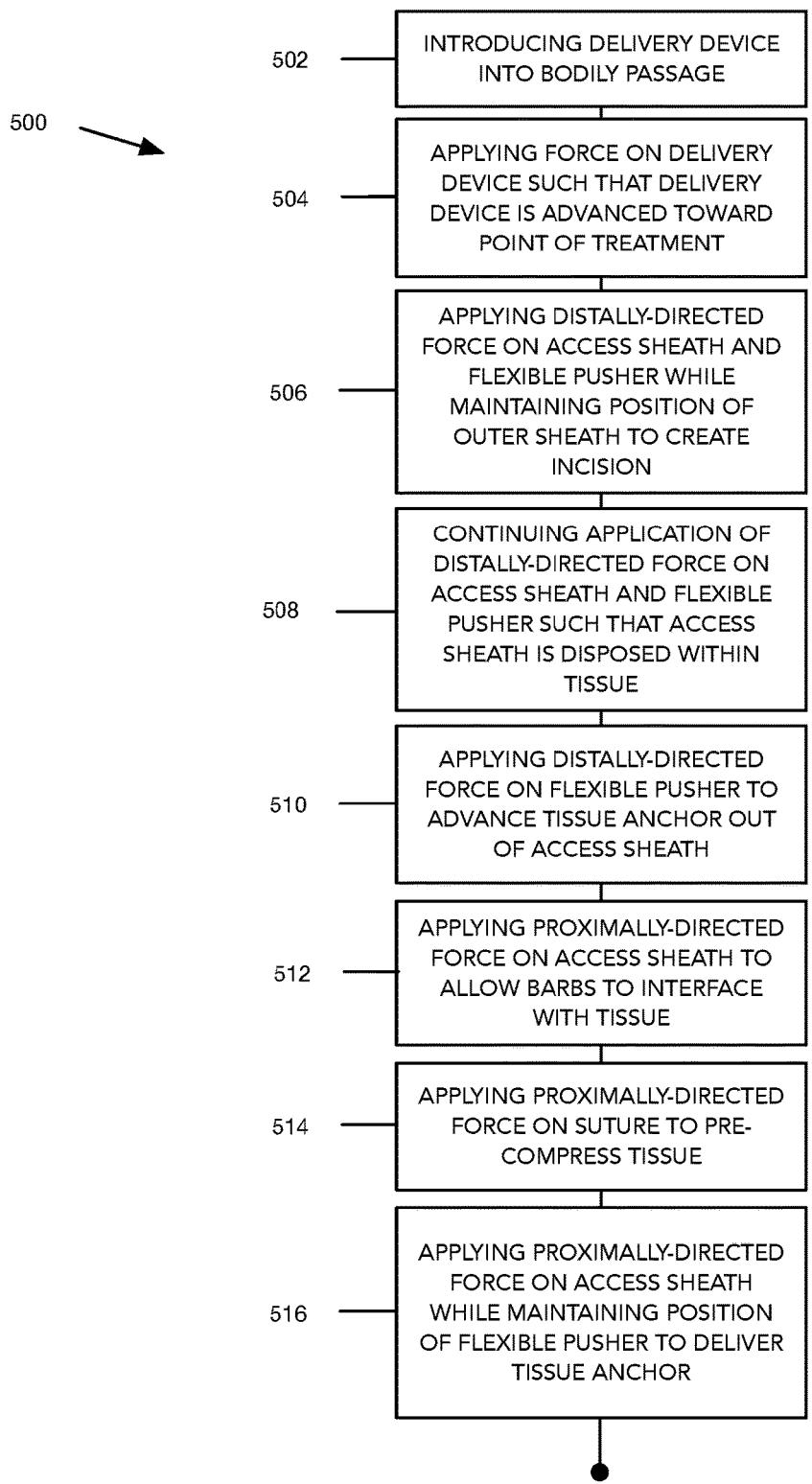
FIG. 19A is a schematic illustration of a portion of another example method of adjusting tissue within the body.
Figure 19B:
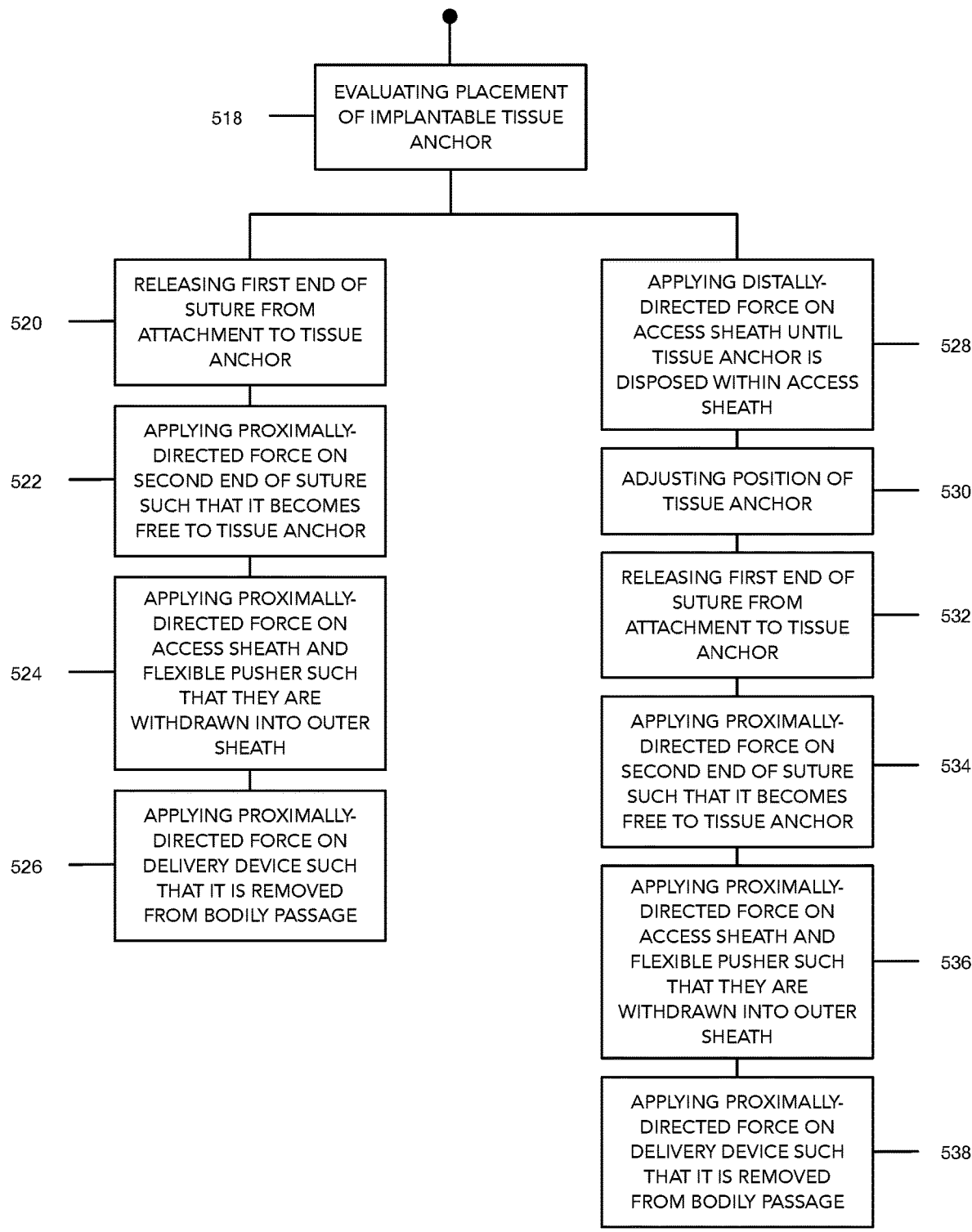
FIG. 19B is a schematic illustration of another portion of the example method of adjusting tissue within the body illustrated in FIG. 19A.

FIGS. 19A and 19B illustrate a schematic illustration of another example method 500 of adjusting tissue within the body using an implantable tissue anchor.

An initial step 502 comprises introducing a delivery device into a bodily passage. The delivery device includes an outer sheath, an access sheath partially disposed within the outer sheath, a flexible pusher partially disposed within the access sheath, an implantable tissue anchor disposed distal to the flexible pusher and within the access sheath, and a suture attached to the implantable tissue anchor and disposed through the flexible pusher. The access sheath has a distal portion that has first, substantially straight configuration when disposed within the outer sheath and a second, curved configuration when free of the outer sheath. The implantable tissue anchor is in the second, compressed configuration. Another step 504 comprises applying a force on the delivery device such that the delivery device is advanced toward a point of treatment. Another step 506 comprises applying a distally-directed force on the access sheath and the flexible pusher while maintaining the position of the outer sheath such that the access sheath is advanced distally relative to the outer sheath and creates an incision in the tissue defining the bodily passage. Another step 508 comprises continuing the application of the distally-directed force on the access sheath and flexible pusher while maintaining the position of the outer sheath such that the access sheath advances into the tissue. Another step 510 comprises applying a distally-directed force on the flexible pusher while maintaining the position of the access sheath such that the tissue anchor advances out of the access sheath and into the tissue a distance equal to about ½ the length of the tissue anchor. Another step 512 comprises applying a proximally-directed force on the access sheath such that the access sheath is partially withdrawn from the tissue and tension is applied to the tissue anchor. Another step 514 comprises applying a proximally-directed force on the suture to pre-compress tissue. Another step 516 comprises applying a proximally-directed force on the access sheath while maintaining the position of the flexible pusher until the tissue anchor becomes free of the access sheath and is disposed within the tissue in the first, expanded configuration.

Another step 518 comprises evaluating the placement of the implantable tissue anchor. If the placement of the implantable tissue anchor is desirable, another step 520 comprises releasing a first end of the suture from attachment to the implantable tissue anchor. Another step 522 comprises applying a proximally-directed force on the second end of the suture such that it becomes free of attachment to the tissue anchor. Another step 524 comprises applying a proximally-directed force on the access sheath and the flexible pusher such that the access sheath and the flexible pusher are withdrawn into the outer sheath. Another step 526 comprises applying a proximally-directed force on the delivery device such that the outer sheath, access sheath, flexible pusher, and suture are withdrawn from the bodily passage. If the placement of the implantable tissue anchor is not desirable, another step 528 comprises applying a distally-directed force on the access sheath until the implantable tissue anchor is disposed within the lumen defined by the access sheath. Another step 530 comprises adjusting the position of the implantable tissue anchor. Another step 532 comprises releasing a first end of the suture from attachment to the implantable tissue anchor. Another step 534 comprises applying a proximally-directed force on the second end of the suture such that it becomes free of attachment to the tissue anchor. Another step 536 comprises applying a proximally-directed force on the access sheath and the flexible pusher such that the access sheath and the flexible pusher are withdrawn into the outer sheath. Another step 538 comprises applying a proximally-directed force on the delivery device such that the outer sheath, access sheath, flexible pusher, and suture are withdrawn from the bodily passage.

Step 502 can be accomplished by introducing a delivery device into any suitable bodily passage and selection of a suitable bodily passage to introduce a delivery device can be based on various considerations, including the treatment intended to be performed. Examples of bodily passages considered suitable to introduce a delivery device include the urethra, an airway, and any other bodily passage considered suitable for a particular embodiment.

Figure 20:
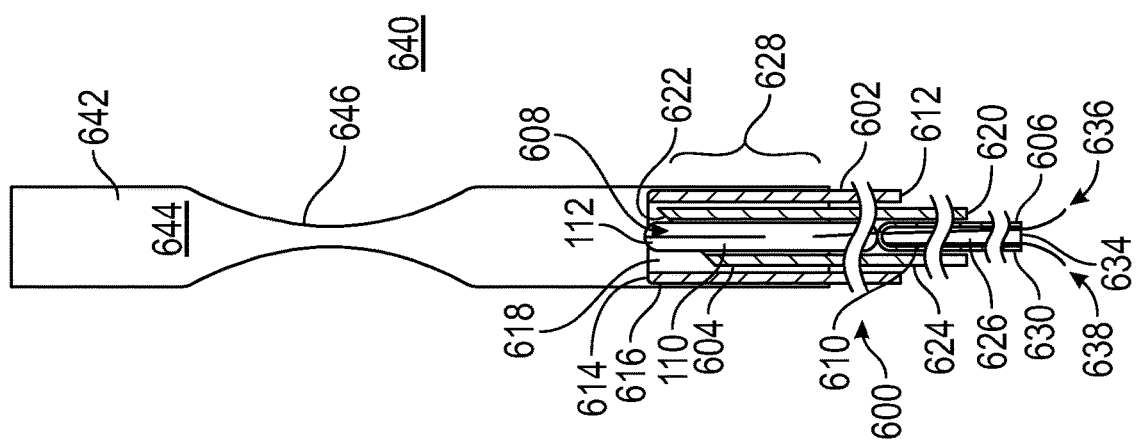
FIG. 20 is a partial elevation view of a delivery device disposed within a bodily passage. The implantable tissue anchor is in the second, compressed configuration.

Step 502 can be accomplished using any suitable delivery device capable of deploying an implantable tissue anchor. An example delivery device 600 is shown in FIGS. 20, 21, 22, 23, 24, and 25. The delivery device 600 includes an outer sheath 602, an access sheath 604 partially disposed within the outer sheath 602, a flexible pusher 606 partially disposed within the access sheath 604, an implantable tissue anchor 608 disposed distal to the flexible pusher 606 and entirely within the access sheath 604, and a suture 610 attached to the implantable tissue anchor 608 and disposed through the flexible pusher 606. The outer sheath 602 has a proximal end 612, a distal end 614, and a main body 616 that defines a lumen 618 that extends from the proximal end 612 to the distal end 614. The access sheath 604 has a proximal end 620, a distal end 622, and a main body 624 that defines a lumen 626, a distal portion 628, and a sharp distal tip 629 that is beveled at a 30 degree angle relative to a lengthwise axis of the access sheath when in the straight configuration. The beveled configuration of the access sheath provides a mechanism for positioning the lumen of the access sheath down-stream from the sharp distal tip 629 during use. The lumen 626 of the access sheath 604 extends from the proximal end 620 to the distal end 622. The distal portion 628 has first, substantially straight configuration when disposed within the outer sheath 602, as shown in FIG. 20, and a second, curved configuration, as shown in FIGS. 21, 22, 23, 24, and 25 when free of the outer sheath 602. In the curved configuration, the distal portion 628 can be defined at any suitable angle relative to a proximal portion of the access sheath 604 that extends proximal to the distal portion 628, such as the angles described herein. The distal cutting tip 629 provides a mechanism for creating an incision into the tissue defining the wall of the bodily passage within which a delivery device has been introduced and to assist with creating an access path for a delivery device and an implantable tissue anchor. The flexible pusher 606 has a proximal end 630, a distal end 632, and a lumen 634 that extends from the proximal end 630 to the distal end 632.

Figure 21:
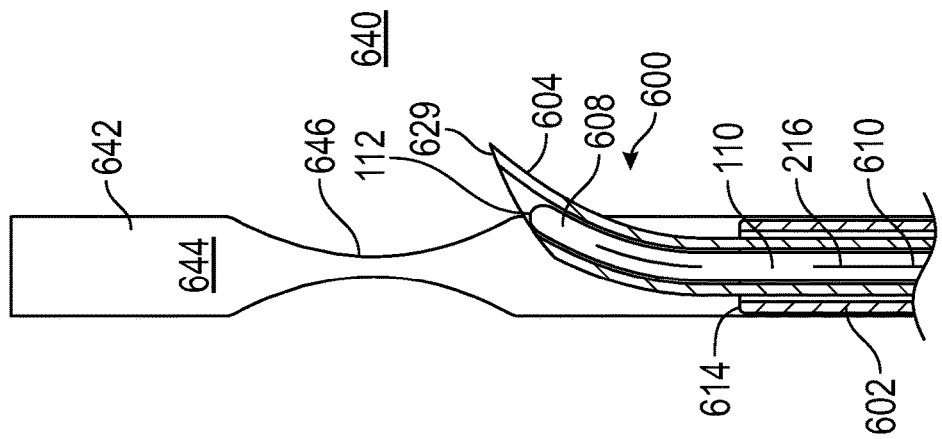
FIG. 21 is a partial elevation view of a delivery device disposed within a bodily passage and partially disposed within tissue. The access sheath is partially disposed within the tissue and the implantable tissue anchor is in the second, compressed configuration.
Figure 22:
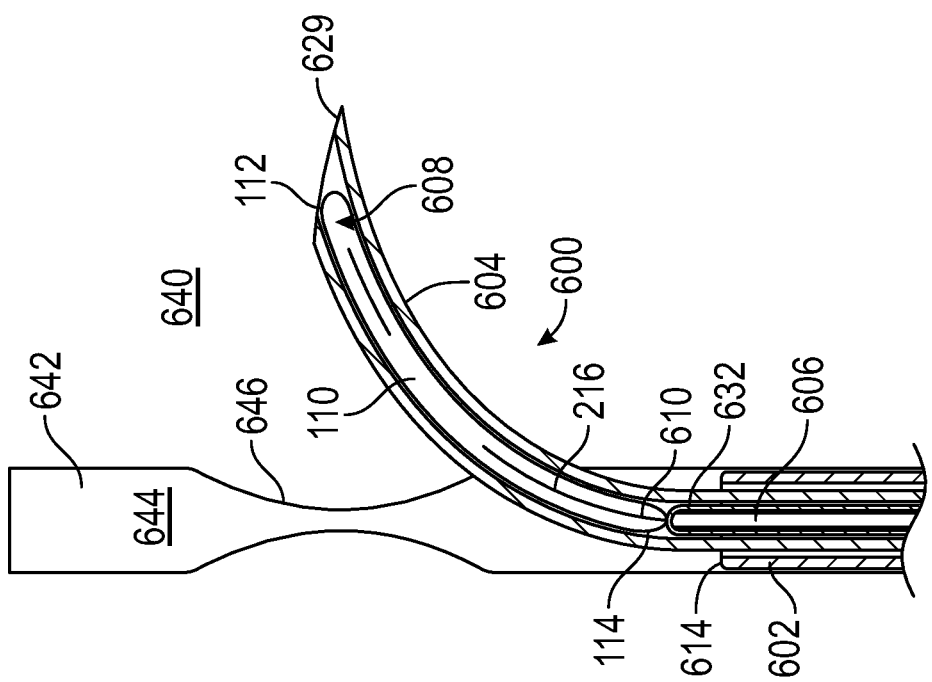
FIG. 22 is a partial elevation view of a delivery device disposed within a bodily passage and partially disposed within tissue. The access sheath is partially disposed within the tissue and the implantable tissue anchor is in the second, compressed configuration.

Step 502 can be accomplished using any suitable implantable tissue anchor and selection of a suitable implantable tissue anchor to utilize in a method can be based on various considerations, such as the treatment intended to be performed. Examples of implantable tissue anchors considered suitable to utilize in a method include implantable tissue anchor 10, implantable tissue anchor 110, variations of the implantable tissue anchors described herein, and any other implantable tissue anchor considered suitable for a particular embodiment. In the illustrated embodiment, implantable tissue anchor 110 is disposed within access sheath 604 and is being deployed within tissue 640. Use of implantable tissue anchor 110 allows for the tissue anchor 110 to be loaded within the delivery device in any orientation as a result of its structural configuration. As shown in FIGS. 20, 21, and 22, the first end 112 of the implantable tissue anchor 110 is disposed within the lumen 626 defined by the access sheath 604.

As shown in FIGS. 22, 23, 24, and 25 the second end 114 of the implantable tissue anchor 110 is disposed adjacent to the distal end 632 of the flexible pusher 606 and within the access sheath 604. As shown in FIG. 20, the suture 610 has a first end 636 and a second end 638. Each of the first and second ends 636, 638 of the suture 610 are disposed proximal to the proximal end 630 of the flexible pusher 606 and the suture 610 extends through the second passageway 216 defined by the implantable tissue anchor 110.

Step 504 can be accomplished by applying any suitable force on any suitable portion of the delivery device such that the delivery device is advanced toward a portion of treatment. For example, a proximal force, a distal force, and/or torque can be applied to the outer sheath 602 such that the entire delivery device is advanced toward a point of treatment. A point of treatment can include any portion, or part of a body, of which it is desired to perform treatment. For example, a point of treatment can include the tissue surrounding a stricture defined within the bodily passage (e.g., urethra) within which the delivery device is positioned, muscular tissue adjacent to a lumen, or an organ such that deployment of an implantable tissue anchor biases the organ to a therapeutic position.

Step 506 is accomplished such that the distal portion of the access sheath defines the second, curved configuration. An incision can be made at any suitable location relative to a point of treatment (e.g., a stricture within the bodily passage). For example, an incision can be made into the urethra or the soft palate and at a point of treatment, proximal to a point of treatment, or distal to a point of treatment, depending on the desired treatment intended to be performed. In addition, step 506 is accomplished such that the flexible pusher and implantable tissue anchor are advanced concurrently with the access sheath. FIG. 21 shows the access sheath 604 advanced distally relative to the outer sheath 602 and the distal cutting tip 629 creating an incision in the tissue 640 defining the bodily passage 642. In the illustrated embodiment, the tissue 640 defines the urethra 644 and a stricture 646 defined within the urethra 644.

Step 508 can be accomplished by advancing the delivery device into any suitable tissue, such as the urethra, the prostate, the soft palate, muscular tissue, and any other tissue considered suitable for a particular treatment. Optionally, step 508 can be accomplished using any suitable technique or method of visualizing the position of the access sheath relative to the tissue defining the bodily passage, such as sonography, and any other technique or method considered suitable for a particular embodiment. In addition, step 508 is accomplished such that the flexible pusher and implantable tissue anchor are advanced concurrently with the access sheath. FIG. 22 shows the access sheath advanced into the tissue.

Figure 23:
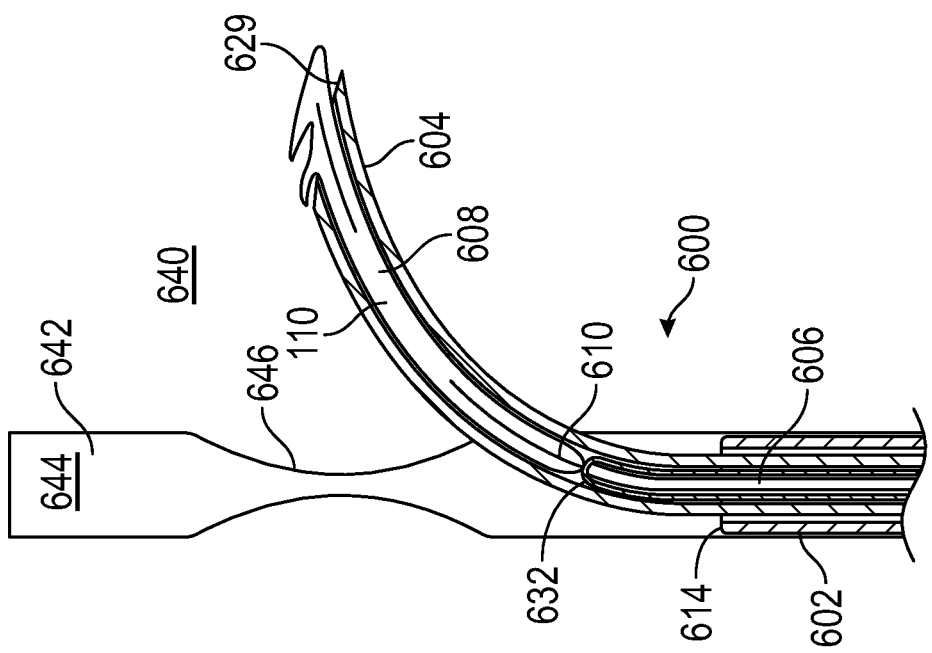
FIG. 23 is a partial elevation view of a delivery device disposed within a bodily passage and partially disposed within tissue. The access sheath is partially disposed within the tissue and the implantable tissue anchor is partially disposed within the tissue.
Figure 24:
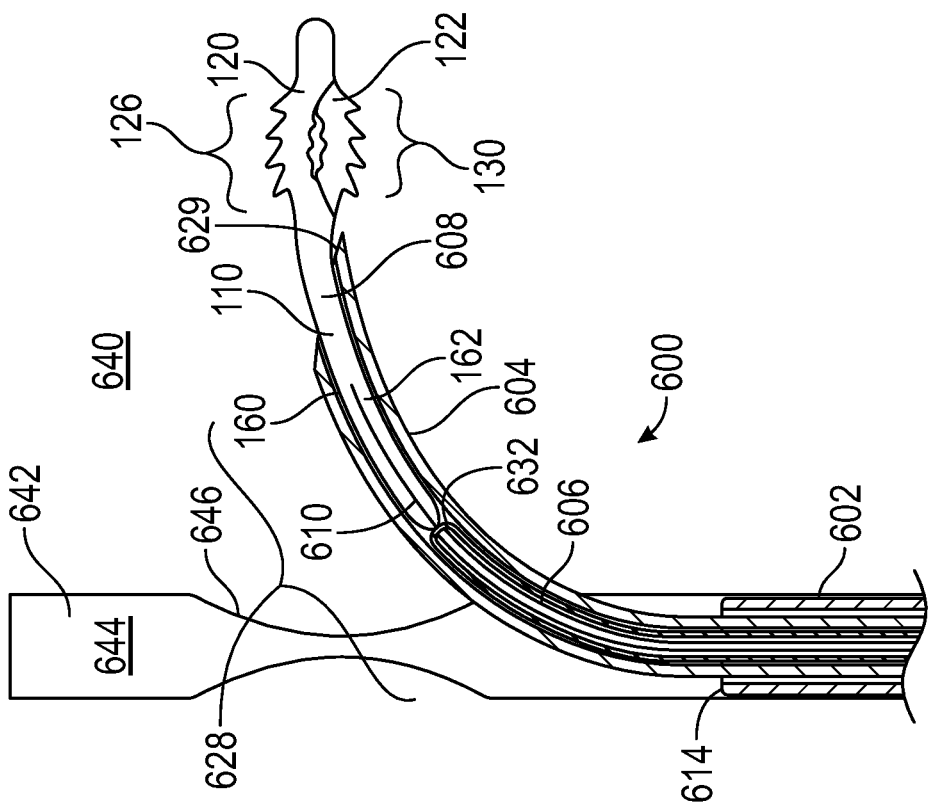
FIG. 24 is a partial elevation view of a delivery device disposed within a bodily passage and partially disposed within tissue. The access sheath is partially disposed within the tissue and the implantable tissue anchor is partially in the first, expanded configuration.

Step 510 allows the implantable tissue anchor to accomplish blunt dissection of the tissue as it is advanced out of the access sheath. FIG. 23 shows the implantable tissue anchor 608 being advance into the tissue 640. FIG. 24 shows ½ of the implantable tissue anchor 608 disposed within the tissue 640 such that the tissue anchor 608 is partially disposed in the first, expanded configuration. In the illustrated embodiment, the first and second arms 120, 122 are disposed in the first, expanded configuration and the third and fourth arms 160, 162 are disposed in the second, compressed configuration. While step 510 has been described as being completed such that the implantable tissue anchor is advanced out of the access sheath and into the tissue a distance equal to ½ the length of the implantable tissue anchor, an implantable tissue anchor can be advanced any suitable distance into the tissue defining the bodily passage. Selection of a suitable distance can be based on various considerations, including the location of a desired deployment site. Examples of distances considered suitable to advance an implantable tissue anchor into tissue that defines a bodily passage include distances equal to ½ the length of an implantable tissue anchor, distances equal to about ½ the length of an implantable tissue anchor, distances that are less than ½ the length of an implantable tissue anchor, distances that are greater than ½ the length of an implantable tissue anchor, distances that are equal to, about, less than, or greater than ¼ the length of an implantable tissue anchor, and any other distance considered suitable for a particular embodiment. In an alternative embodiment, an alternative step comprises applying a proximally-directed force on the access sheath while maintaining the position of the outer sheath and flexible pusher such that the access sheath is withdrawn into the outer sheath and from the tissue a distance equal to about ½ the length of the implantable tissue anchor can be completed prior to step 510 such that the access sheath creates the path within which the implantable tissue anchor can be disposed. Optionally, step 510 can be accomplished using any suitable technique or method of visualizing the position of the implantable tissue anchor relative to the access sheath and/or tissue defining the bodily passage, such as sonography, and any other technique or method considered suitable for a particular embodiment.

Step 512 provides a mechanism for allowing the first and second plurality of barbs 126, 130 to become embedded within the tissue 640. For example, step 512 can be accomplished such that a proximally-directed force is applied on the access sheath such that the access sheath is partially withdrawn from over the implant allowing a portion of a tissue anchor (e.g., length described herein, lengths described in step 510) to be exposed to the tissue and the barbs contact the tissue.

Step 514 provides a mechanism to pre-compress the tissue disposed between the first and second plurality of barbs 126, 130 and the access sheath 604.

Figure 25:
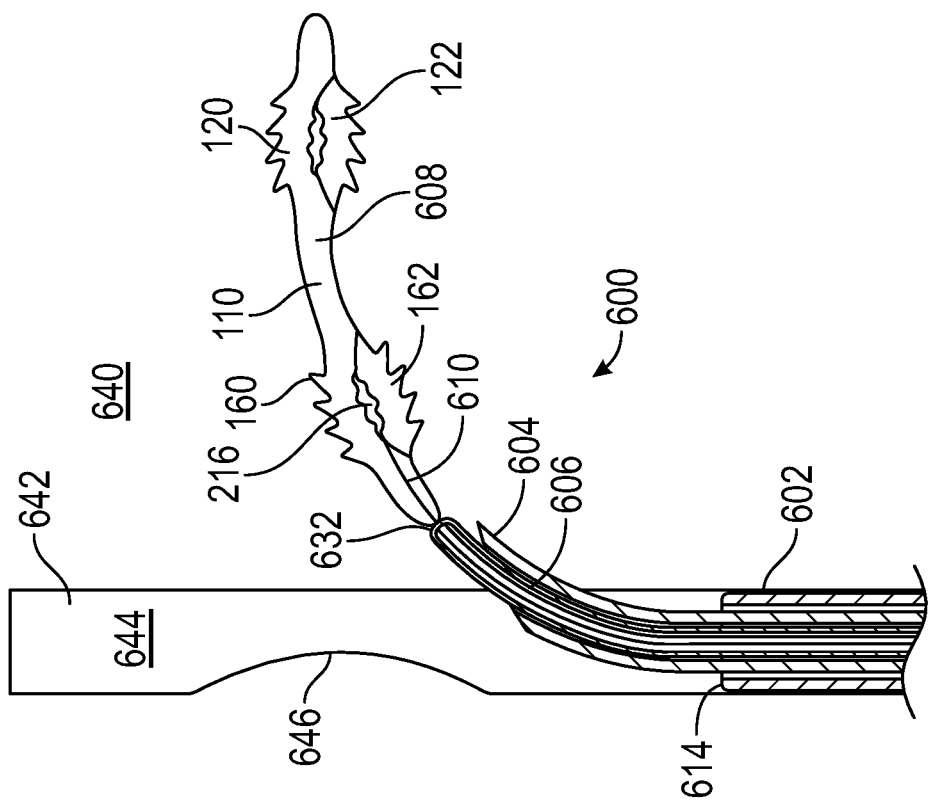

Step 516 is accomplished such that the entire implantable tissue anchor is disposed in the first, expanded configuration. In the illustrated embodiment, the first, second, third, and fourth arms 120, 122, 160, 162 are disposed in the first, expanded configuration. FIG. 25 shows the implantable tissue anchor 608 free of the access sheath 604 and the stricture 646 being treated on the side of the urethra 640 within which the implantable tissue anchor 608 has been deployed. The implantable tissue anchor 608 is in the first, expanded configuration such that the tissue is expanded between the first and second arms and between the third and fourth arms such that the tissue at the point of treatment becomes compressed and widens the bodily passage (e.g., foreshortening compresses walls of the tissue within which it is deployed). Optionally, step 516 can be accomplished while maintaining the position of the outer sheath.

Step 518 can be accomplished using any suitable technique or method of visualizing the position of the implantable tissue anchor relative to the tissue defining the bodily passage, such as sonography, and any other technique or method considered suitable for a particular embodiment.

Step 520 can be accomplished by releasing any force being applied on the first end of the suture, or any portion of the suture disposed between the first end and the implantable tissue anchor.

Step 522 can be accomplished by applying a proximally directed force on the second end of the suture, or any portion of the suture disposed between the second end and the implantable tissue anchor until the suture is withdrawn from the passageway 216, lumen 634, and/or the bodily passage.

Step 524 provides a mechanism for positioning the access sheath in the first, straight configuration and preventing the access sheath and flexible pusher from damaging tissue as the delivery device is withdrawn from the bodily passage in step 526. Optionally, step 524 can be accomplished while maintaining the position of the outer sheath.

Step 526 can be accomplished by applying a proximally directed force on any suitable portion of the delivery device to withdraw the outer sheath, access sheath, flexible pusher, and suture from the bodily passage.

Figure 27:
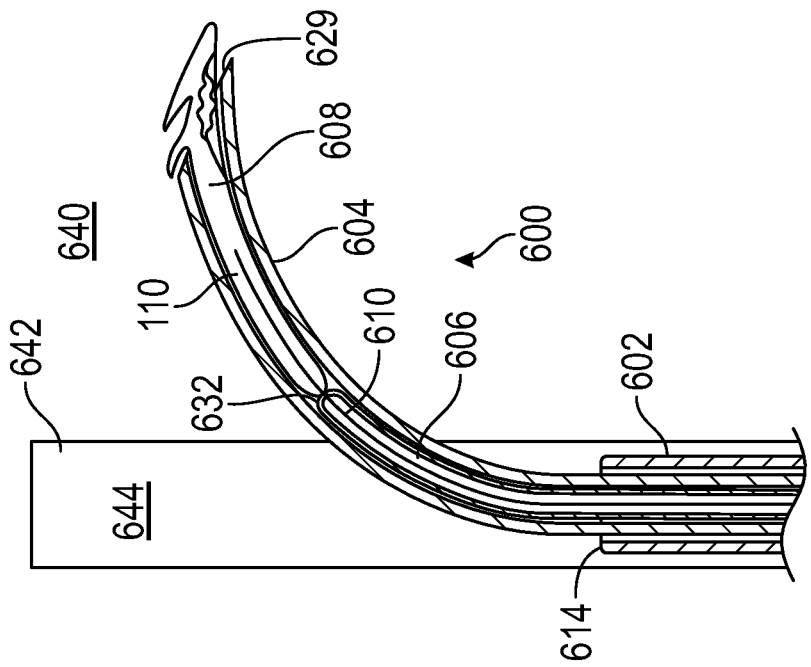
FIG. 27 is a partial elevation view of a delivery device disposed within a bodily passage and partially disposed within tissue. The access sheath is partially disposed within the tissue and the implantable tissue anchor is partially in the first, expanded configuration.
Figure 26:
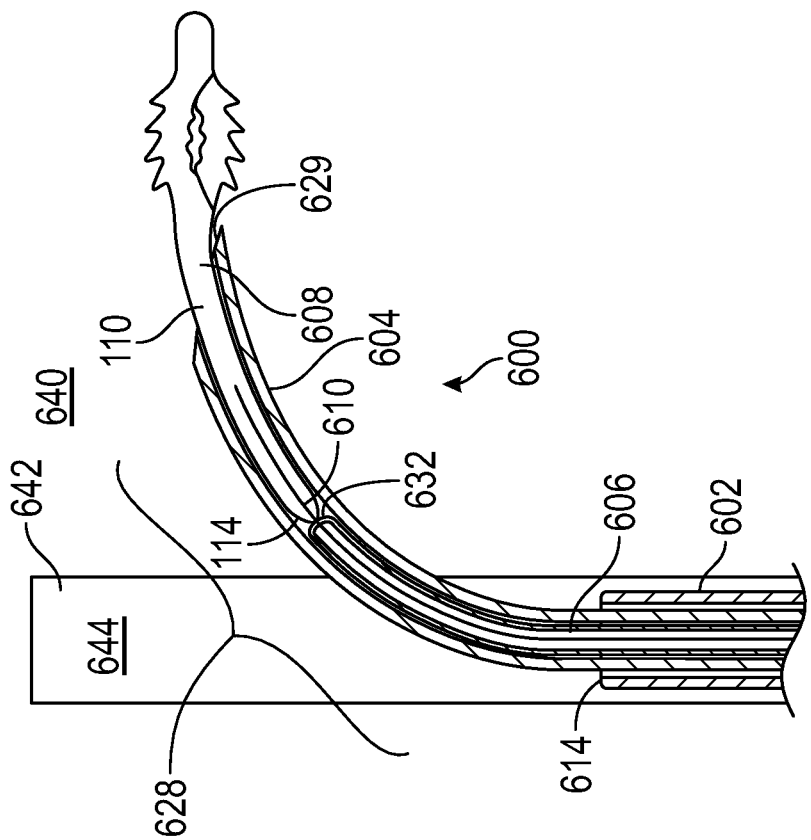
FIG. 26 is a partial elevation view of a delivery device disposed within a bodily passage and partially disposed within tissue. The access sheath is partially disposed within the tissue and the implantable tissue anchor is partially in the first, expanded configuration.
Figure 28:
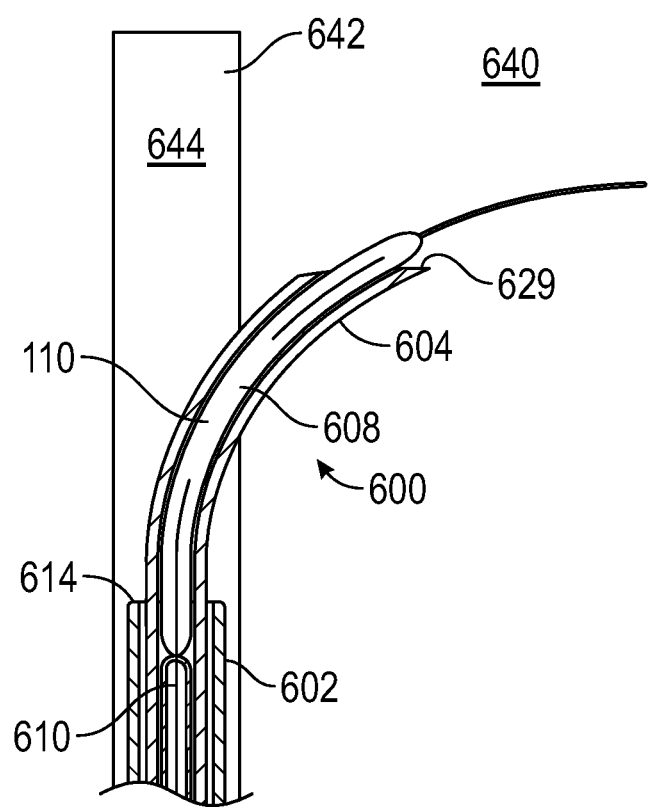
FIG. 28 is a partial elevation view of a delivery device disposed within a bodily passage and partially disposed within tissue. The access sheath is partially disposed within the tissue and the implantable tissue anchor is in the second, compressed configuration.

Step 528 can be accomplished until the entire implantable tissue anchor is disposed within the access sheath. FIGS. 26 and 27 show the access sheath 604 being advanced distally over the implantable tissue anchor 608. FIG. 28 shows the access sheath 604 entirely disposed over the implantable tissue anchor 608. Depending on the adjustment being made to the implantable tissue anchor, an alternative step can comprise applying a distally-directed force on the access sheath while maintaining the position of the outer sheath until a portion of an implantable tissue anchor (e.g., third and fourth arms 160, 162) is disposed within the lumen defined by the access sheath. Optionally, step 528 can be accomplished while applying a distally-directed force on the suture such that the implantable tissue anchor is pulled into the access sheath. Optionally, step 528 can be accomplished while maintaining the position of the outer sheath. Optionally, step 528 can be accomplished while maintaining tension on the first end and/or second end of the suture.

Step 530 can be accomplished by applying any suitable force on any suitable portion of the delivery device such that the position of the delivery device and/or implantable tissue anchor is disposed at a desired location. For example, a proximal force, a distal force, and/or torque can be applied to the outer sheath 602 and/or access sheath 604 and/or any of the steps described herein can be completed. Optionally, each of step 510, step 512, step 514, and/or step 516 can be repeated to complete step 530 or subsequent to step 530.

Step 532 can be accomplished by releasing any force being applied on the first end of the suture, or any portion of the suture disposed between the first end and the implantable tissue anchor.

Step 534 can be accomplished by applying a proximally directed force on the second end of the suture, or any portion of the suture disposed between the second end and the implantable tissue anchor until the suture is withdrawn from the passageway 216 and/or the bodily passage.

Step 536 provides a mechanism for positioning the access sheath in the first, straight configuration and preventing the access sheath and flexible pusher from damaging tissue as the delivery device is withdrawn from the bodily passage in step 538. Optionally, step 536 can be accomplished while maintaining the position of the outer sheath.

Step 538 can be accomplished by applying a proximally directed force on any suitable portion of the delivery device to withdraw the outer sheath, access sheath, flexible pusher, and suture from the bodily passage.

Any of the steps described in method 500 can be repeated any suitable number of times. For example, in treatments in which it is desired to deploy more than one implantable tissue anchor, method 500 can be repeated with a second implantable tissue anchor, which can be back loaded into the access sheath by removing the flexible pusher, inserting the second implantable tissue anchor into the lumen defined by the access sheath, and then inserting the flexible pusher into the access sheath and distal to the second implantable tissue anchor. Utilizing the implantable tissue anchors described herein and the methods described herein are considered advantageous at least because they do not require full perforation between an interior surface and exterior surface (e.g., first and second walls of a portion of a body (e.g., vessel, prostate)) to implant the tissue anchor (e.g., the implantable tissue anchors can be deployed in tissue having any thickness), the tissue anchors can be deployed to treat any suitable bodily passage, the tissue anchors can be deployed at any suitable angle within the tissue, and the bias of the tissue anchor is utilized to compress the tissue and address any narrowing of bodily passages adjacent to where the tissue anchor has been deployed (e.g., reduce or eliminate stricture within bodily passage). In addition, the implantable tissue anchors provide a mechanism for treating various conditions, such as OSA, benign prostatic hyperplasia, and any other condition considered suitable for a particular embodiment.

Figure 29:
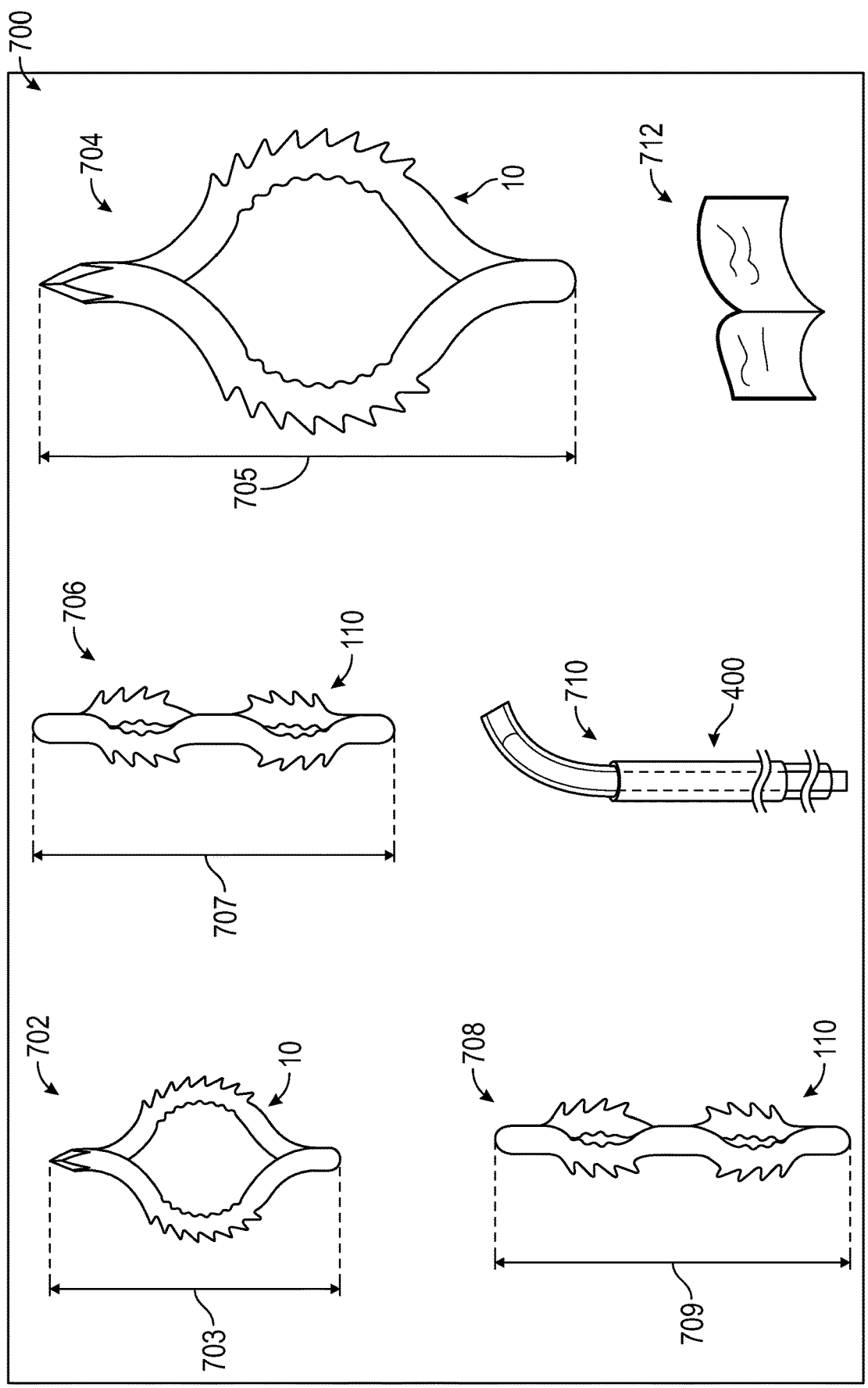
FIG. 29 illustrates an example kit that includes a plurality of implantable tissue anchors and a delivery device.

FIG. 29 illustrates an exemplary kit 700 comprising a first implantable tissue anchor 702 according to an embodiment, such as implantable tissue anchor 10 illustrated in FIG. 1; a second implantable tissue anchor 704 according to an embodiment, such as implantable tissue anchor 10 illustrated in FIG. 1; a third implantable tissue anchor 706 according to an embodiment, such as implantable tissue anchor 110 illustrated in FIG. 7; a fourth implantable tissue anchor 708 according to an embodiment, such as implantable tissue anchor 110 illustrated in FIG. 7; a delivery device 710 for deploying an implantable tissue anchor according to an embodiment, such as delivery device 400 illustrated in FIG. 13; and instructions for use 712. In the illustrated embodiment, the first implantable tissue anchor 702 has a first length 703, the second implantable tissue anchor 704 has a second length 705 that is greater than the first length 705, the third implantable tissue anchor 706 has a third length 707, and the fourth implantable tissue anchor 708 has a fourth length 709 that is greater than the third length 707.

While the kit 700 has been illustrated as including four implantable tissue anchors 702, 704, 706, 708, and a delivery device 710 for deploying an implantable tissue anchor, any suitable number, and type, of implantable tissue anchors and/or delivery devices can be included in a kit. Selection of a suitable number of implantable tissue anchors and/or delivery devices to include in a kit according to a particular embodiment can be based on various considerations, such as the treatment intended to be performed. Examples of numbers of implantable tissue anchors and/or delivery devices considered suitable to include in a kit include at least one, one, two, a plurality, three, four, five, six, seven, eight, nine, ten, more than ten, and any other number considered suitable for a particular embodiment.

Furthermore, while implantable tissue anchor 10, implantable tissue anchor 110, and delivery device 400 have been illustrated as included in kit 700, any suitable implantable tissue anchor and/or delivery device can be included in a kit. Selection of a suitable implantable tissue anchor and/or delivery device to include in a kit according to a particular embodiment can be based on various considerations, such as the treatment intended to be performed. Examples of implantable tissue anchors and delivery devices considered suitable to include in a kit include implantable tissue anchor 10, implantable tissue anchor 110, delivery device 400, delivery device 600, and/or any other implantable tissue anchor and/or delivery device considered suitable for a particular embodiment.

Those with ordinary skill in the art will appreciate that various modifications and alternatives for the described and illustrated examples can be developed in light of the overall teachings of the disclosure, and that the various elements and features of one example described and illustrated herein can be combined with various elements and features of another example without departing from the scope of the invention. Accordingly, the particular arrangement of elements and steps disclosed herein have been selected by the inventor(s) simply to describe and illustrate examples of the invention and are not intended to limit the scope of the invention or its protection, which is to be given the full breadth of the appended claims and any and all equivalents thereof.

What is claimed is:

1. An implantable tissue anchor moveable between a first, expanded configuration and a second, compressed configuration, the implantable tissue anchor comprising:

a first end, a second end, a lengthwise axis, and a main body, the main body defining a first arm, a second arm, a first plurality of recesses on the first arm, a first plurality of barbs on the first arm, a second plurality of recesses on the second arm, and a second plurality of barbs on the second arm, each of the first end and the second end disposed on the lengthwise axis, the lengthwise axis disposed between the first plurality of barbs and the second plurality of recesses in the first, expanded configuration, the main body having a first length along the lengthwise axis in the first, expanded configuration and a second length along the lengthwise axis in the second, compressed configuration that is greater than the first length;

the first arm and the second arm defining a first closed loop and a first passageway extending through the main body when said implantable tissue anchor is in the first, expanded configuration, each barb of the first plurality of barbs extending from the first arm and away from the first passageway;

a first barb of the first plurality of barbs partially disposed within a first recess of the second plurality of recesses when said implantable tissue anchor is in the second, compressed configuration; and a first barb of the second plurality of barbs partially disposed within a first recess of the first plurality of recesses when said implantable tissue anchor is in the second, compressed configuration.

2. The implantable tissue anchor of claim 1, wherein the main body defines a cutting tip on the first end.

3. The implantable tissue anchor of claim 1, wherein each of the first plurality of barbs and the second plurality of barbs includes less than sixteen barbs.

4. The implantable tissue anchor of claim 1, wherein each of the first plurality of recesses and the second plurality of recesses includes less than sixteen recesses.

5. The implantable tissue anchor of claim 1, wherein the main body is formed of high-density polyethylene.

6. The implantable tissue anchor of claim 1, further including an echogenic material disposed within the main body.

7. The implantable tissue anchor of claim 1, wherein the main body defines a proximal terminus, and a distal terminus, the first and second arms terminating in the proximal terminus and the distal terminus.

8. The implantable tissue anchor of claim 7, wherein the proximal terminus is a structural junction of two portions of a monolithic structure.

9. The implantable tissue anchor of claim 7, wherein the distal terminus is a structural junction of two portions of a monolithic structure.

10. The implantable tissue anchor of claim 1, wherein the main body defines a third arm, a fourth arm, a third plurality of recesses on the third arm, a third plurality of barbs on the third arm, a fourth plurality of recesses on the fourth arm, and a fourth plurality of barbs on the fourth arm.

11. The implantable tissue anchor of claim 10, wherein the third arm and the fourth arm define a second closed loop and a second passageway that extends through the main body when said implantable tissue anchor is in the first, expanded configuration.

12. The implantable tissue anchor of claim 10, wherein a first barb of the third plurality of barbs is partially disposed within a first recess of the fourth plurality of recesses when said implantable tissue anchor is in the second, compressed configuration; and
  a first barb of the fourth plurality of barbs is partially disposed within a first recess of the third plurality of recesses when said implantable tissue anchor is in the second, compressed configuration.

13. The implantable tissue anchor of claim 10, wherein the main body defines a proximal terminus, an intermediate terminus, and a distal terminus, the first and second arms terminating in the proximal terminus and the intermediate terminus, and the third and fourth arms terminating in the intermediate terminus and the distal terminus.

14. The implantable tissue anchor of claim 1, wherein the first end is a blunt end and the second end is a blunt end.

15. An implantable tissue anchor moveable between a first, expanded configuration and a second, compressed configuration, the implantable tissue anchor comprising:
  a first end, a second end, a lengthwise axis, and a main body, the main body defining a first arm, a second arm, a third arm, a fourth arm, a first plurality of recesses on the first arm, a first plurality of barbs on the first arm, a second plurality of recesses on the second arm, a second plurality of barbs on the second arm, a third plurality of recesses on the third arm, a third plurality of barbs on the third arm, a fourth plurality of recesses on the fourth arm, and a fourth plurality of barbs on the fourth arm, each of the first end and the second end disposed on the lengthwise axis, the lengthwise axis disposed between the first plurality of barbs and the second plurality of recesses in the first, expanded configuration, the main body having a first length along the lengthwise axis in the first, expanded configuration and a second length along the lengthwise axis in the second, compressed configuration that is greater than the first length;
  the first arm and the second arm defining a first closed loop and a first passageway extending through the main body when said implantable tissue anchor is in the first, expanded configuration, each barb of the first plurality of barbs extending from the first arm and away from the first passageway;
  the third arm and the fourth arm defining a second closed loop and a second passageway extending through the main body when said implantable tissue anchor is in the first, expanded configuration;
  a first barb of the first plurality of barbs partially disposed within a first recess of the second plurality of recesses when said implantable tissue anchor is in the second, compressed configuration;
  a first barb of the second plurality of barbs partially disposed within a first recess of the first plurality of recesses when said implantable tissue anchor is in the second, compressed configuration;
  a first barb of the third plurality of barbs partially disposed within a first recess of the fourth plurality of recesses when said implantable tissue anchor is in the second, compressed configuration; and
  a first barb of the fourth plurality of barbs partially disposed within a first recess of the third plurality of recesses when said implantable tissue anchor is in the second, compressed configuration.

16. The implantable tissue anchor of claim 15, wherein each of the first plurality of barbs, the second plurality of barbs, the third plurality of barbs, and the fourth plurality of barbs includes less than sixteen barbs.

17. The implantable tissue anchor of claim 15, wherein each of the first plurality of recesses, the second plurality of recesses, the third plurality of recesses, and the fourth plurality of recesses includes less than sixteen recesses.

18. The implantable tissue anchor of claim 15, further including an echogenic material disposed within the main body.

* * * * *